US012349978B2

(12) United States Patent
Upadrasta et al.

(10) Patent No.: US 12,349,978 B2
(45) Date of Patent: Jul. 8, 2025

(54) AUTO-CONFIGURABLE SIMULATION SYSTEM AND METHOD

(71) Applicant: Intuitive Surgical Operations, Inc., Sunnyvale, CA (US)

(72) Inventors: Prasad V. Upadrasta, San Jose, CA (US); Anusha Balan, San Jose, CA (US); Joey Chau, Cupertino, CA (US); Quang Tonthat, San Jose, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 640 days.

(21) Appl. No.: 17/635,165

(22) PCT Filed: Aug. 14, 2020

(86) PCT No.: PCT/US2020/046460
§ 371 (c)(1),
(2) Date: Feb. 14, 2022

(87) PCT Pub. No.: WO2021/034694
PCT Pub. Date: Feb. 25, 2021

(65) Prior Publication Data
US 2022/0273368 A1 Sep. 1, 2022

Related U.S. Application Data

(60) Provisional application No. 62/888,298, filed on Aug. 16, 2019.

(51) Int. Cl.
*A61B 34/10* (2016.01)
*A61B 34/00* (2016.01)
(Continued)

(52) U.S. Cl.
CPC .............. *A61B 34/10* (2016.02); *A61B 34/25* (2016.02); *A61B 34/35* (2016.02); *A61B 34/37* (2016.02);
(Continued)

(58) Field of Classification Search
CPC ......... A61B 34/10; A61B 34/25; A61B 34/35; A61B 34/37; A61B 34/70; A61B 90/36;
(Continued)

(56) References Cited

U.S. PATENT DOCUMENTS

2004/0161731 A1* 8/2004 Arington .................. G09B 7/04
434/262
2014/0272863 A1* 9/2014 Kim ....................... G06T 19/006
434/262
2016/0210882 A1* 7/2016 Gulasy ................... G09B 23/28

FOREIGN PATENT DOCUMENTS

WO WO-2012151585 A2 11/2012
WO WO-2015095715 A1 6/2015

OTHER PUBLICATIONS

International Preliminary Report on Patentability for Application No. PCT/US2020/046460, mailed Mar. 3, 2022, 9 pages.
(Continued)

*Primary Examiner* — Said Broome
*Assistant Examiner* — Andrew Shin

(57) ABSTRACT

An exemplary auto-configurable simulation system includes a control module configured to simulate a first type of surgical instrument manipulating system included in a plurality of types of surgical instrument manipulating systems and a computing device communicatively connected to the control module. The computing device includes a processor configured to execute instructions to communicatively connect the control module to a user control console of a computer-assisted surgical system, determine, after communicatively connecting the control module to the user control
(Continued)

console, that the user control console is configured to facilitate control of a second type of surgical instrument manipulating system, store data indicating that the user control console is configured to facilitate control of the second type of surgical instrument manipulating system, and reprogram the control module such that the control module is configured to simulate the second type of surgical instrument manipulating system.

19 Claims, 12 Drawing Sheets

(51) Int. Cl.
*A61B 34/35* (2016.01)
*A61B 34/37* (2016.01)
*A61B 90/00* (2016.01)

(52) U.S. Cl.
CPC .............. *A61B 34/70* (2016.02); *A61B 90/36* (2016.02); *A61B 2034/102* (2016.02); *A61B 2090/365* (2016.02)

(58) Field of Classification Search
CPC ........ A61B 2034/102; A61B 2090/365; A61B 2034/101; A61B 2034/302; G09B 23/285; G16H 40/60
See application file for complete search history.

(56) References Cited

OTHER PUBLICATIONS

International Search Report and Written Opinion for Application No. PCT/US2020/046460, mailed Oct. 11, 2020, 11 pages.
Vertut, J, and Coiffet, P., "Robot Technology: Teleoperation and Robotics Evolution and Development," English translation, Prentice-Hall, Inc., Inglewood Cliffs, NJ, USA 1986, vol. 3A, 332 pages.

\* cited by examiner

AUTO-CONFIGURABLE SIMULATION SYSTEM AND METHOD

RELATED APPLICATIONS

The present application is a U.S. National Stage Application under 35 U.S.C. § 371 of International Application No. PCT/US2020/046460, filed on Aug. 14, 2020, which claims priority to U.S. Provisional Patent Application No. 62/888,298, filed on Aug. 16, 2019, the contents of which are hereby incorporated by reference in their entirety.

BACKGROUND INFORMATION

A computer-assisted surgical system that employs robotic and/or teleoperation technology typically includes a stereoscopic image viewer configured to provide, for display to a surgeon, imagery of a surgical space as captured by an endoscope. While the surgeon's eyes are positioned in front of viewing lenses of the stereoscopic image viewer, the surgeon may view the imagery of the surgical space while remotely manipulating one or more surgical instruments located within the surgical space. The surgical instruments are attached to one or more manipulator arms of a surgical instrument manipulating system included as part of the computer-assisted surgical system.

Advances in computer-assisted surgical systems have resulted in a variety of different types of computer-assisted surgical systems being developed. Each type of computer-assisted surgical system may be configured differently, controlled differently, and/or may have unique features adapted to perform specific types of operations within the surgical space. For example, a first type of computer-assisted surgical system may include a first type of surgical instrument manipulating system in which multiple manipulator arms are configured and/or operate in a first manner, and a second type of computer-assisted surgical system may include a second type of surgical instrument manipulating system in which one or more manipulator arms are configured and/or operate in a second manner different from the first manner.

The differences between the various types of computer-assisted surgical systems result in different operating conditions experienced by a surgeon and often different required skillsets to perform surgical procedures. Accordingly, training systems have been developed that allow a surgeon to quickly and effectively learn how to operate the different types of computer-assisted surgical systems. However, conventional training systems for computer-assisted surgical systems typically require that separate, system-specific simulation systems be developed that are specifically adapted for use with the different types of computer-assisted surgical system. For example, a first system-specific simulation system is required for a first type of computer-assisted surgical system that includes a first type of surgical instrument manipulating system, and a second system-specific simulation system that is different from the first system-specific simulation system is required for a second type of computer-assisted surgical system that includes a second type of surgical instrument manipulating system. However, providing a different system-specific simulation system for each type of computer-assisted surgical system may be inefficient and/or cost prohibitive, especially for facilities (e.g., hospitals) that have multiple different types of computer-assisted surgical systems.

SUMMARY

An exemplary auto-configurable simulation system comprises a control module configured to simulate a first type of surgical instrument manipulating system included in a plurality of types of surgical instrument manipulating systems; and a computing device communicatively connected to the control module, the computing device including: a memory storing instructions; and a processor communicatively connected to the memory and configured to execute the instructions to: communicatively connect the control module to a user control console of a computer-assisted surgical system; determine, after communicatively connecting the control module to the user control console, that the user control console is configured to facilitate control of a second type of surgical instrument manipulating system included in the plurality of types of surgical instrument manipulating systems; store data indicating that the user control console is configured to facilitate control of the second type of surgical instrument manipulating system; and reprogram the control module such that the control module is configured to simulate the second type of surgical instrument manipulating system.

An additional exemplary auto-configurable simulation system comprises a memory storing instructions; and a processor communicatively connected to the memory and configured to execute the instructions to: communicatively connect a control module to a user control console that includes an input device and a display device, the control module configured to simulate a first type of surgical instrument manipulating system included in a plurality of types of surgical instrument manipulating systems; determine, after communicatively connecting the control module to the user control console, that the user control console is configured to facilitate control of a second type of surgical instrument manipulating system included in the plurality of types of surgical instrument manipulating systems; store data indicating that the user control console is configured to facilitate control of the second type of surgical instrument manipulating system; reprogram the control module such that the control module is configured to simulate the second type of surgical instrument manipulating system; and provide, based on the reprogrammed control module, a virtual environment for display by the display device of the user control console, the virtual environment including a virtual instrument that is movable in response to movement of the input device of the user control console for performing a simulated procedure in the virtual environment.

An exemplary method comprises determining, by an auto-configurable simulation system after a control module configurable to simulate one of a plurality of types of surgical instrument manipulating systems is communicatively connected to a user control console, that the user control console is configured to facilitate control of a first type of surgical instrument manipulating system included in the plurality of types of surgical instrument manipulating systems; determining, by the auto-configurable simulation system, whether the control module is currently configured to simulate the first type of surgical instrument manipulating system included in the plurality of types of surgical instrument manipulating systems, and reprogramming, by the auto-configurable simulation system when it is determined that the control module is not currently configured to simulate the first type of surgical instrument manipulating system, the control module such that the control module is configured to simulate the first type of surgical instrument manipulating system.

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

DETAILED DESCRIPTION

Figure 1:
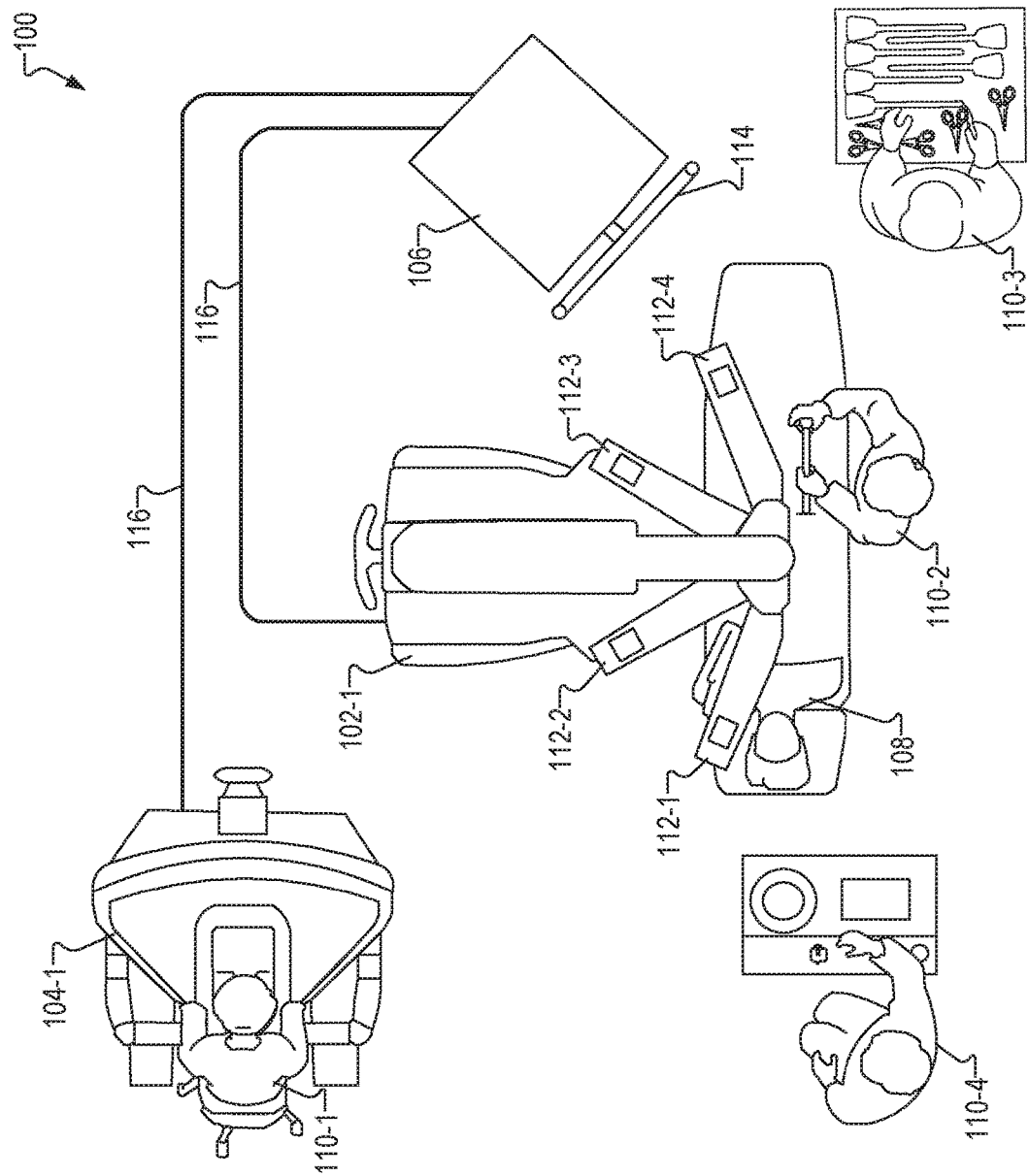
FIG. 1 illustrates an exemplary computer-assisted surgical system according to principles described herein.

Auto-configurable simulation systems and methods are described herein. As will be described in more detail below, an exemplary auto-configurable simulation system includes a control module configured to simulate a first type of surgical instrument manipulating system included in a plurality of types of surgical instrument manipulating systems and a computing device communicatively connected to the control module. The computing device includes a memory that stores instructions and a processor communicatively connected to the memory. The processor of the exemplary auto-configurable simulation system is configured to execute the instructions to communicatively connect the control module to a user control console of a computer-assisted surgical system, and determine, after communicatively connecting the control module to the user control console, that the user control console is configured to facilitate control of a second type of surgical instrument manipulating system included in the plurality of types of surgical instrument manipulating systems. The processor is further configured to store data indicating that the user control console is configured to facilitate control of the second type of surgical instrument manipulating system, and reprogram the control module such that the control module is configured to simulate the second type of surgical instrument manipulating system.

Based on the reprogramming of the control module, the processor may be further configured to provide a virtual environment for display by a display device (e.g., a stereoscopic or monoscopic image viewer) of the user control console. The virtual environment may include a virtual surgical instrument (e.g., virtual forceps, a virtual cutting instrument, etc.) that is movable in response to movement of an input device (e.g., foot pedals, buttons, switches, etc.) of the user control console for performing a simulated procedure in the virtual environment (e.g., for training purposes). Exemplary virtual environments are described herein.

Various advantages and benefits are associated with the systems and methods described herein. For example, auto-configurable simulation systems and methods such as those described herein allow an operator (e.g., a surgeon) to use the same control interfaces and input devices during a simulated procedure as would be used during an actual surgical procedure. In addition, auto-configurable simulation systems such as those described herein are configured to communicate with and provide training simulations for any one of a plurality of different types of computer-assisted surgical systems. As such, a facility (e.g., a hospital) that has a plurality of different types of computer-assisted surgical systems only needs to purchase/lease one auto-configurable simulation system to be used with the plurality of different types of computer-assisted surgical systems, which reduces cost to the facility. Further, because the exemplary systems and methods described herein are auto-configurable, personnel (e.g., nurses, surgical assistants, etc.) at such facilities do not need to know the type and/or configuration of a particular computer-assisted surgical system to be simulated prior to using an auto-configurable simulation system, which increases ease of use. These and other benefits that may be realized by the systems and methods described herein will be evident from the disclosure that follows.

The exemplary auto-configurable simulation systems described herein are configured to operate as part of or in conjunction with any one of a plurality of different types of computer-assisted surgical systems. The plurality of different types of computer-assisted surgical systems may be of different types at least because they include different types of surgical instrument manipulating systems. For example, a first computer-assisted surgical system may include a first type of surgical instrument manipulating system, a second computer-assisted surgical system may include a second type of surgical instrument manipulating system, and a third computer-assisted surgical system may include a third type of surgical instrument manipulating system.

Each type of surgical instrument manipulating system may have a different architecture (e.g., manipulator arm architecture), have a different kinematic profile, and/or operate according to different configuration parameters. As such, exemplary auto-configurable simulation systems such as those described herein are configured to automatically reconfigure themselves to be able to communicate with, control, and/or provide simulated procedures associated with any one of a plurality of different types of computer-assisted surgical systems having different types of surgical instrument manipulating systems. As used herein, the expression "automatically" means that an operation (e.g., reprogramming of a control module) or series of operations are performed without requiring further input from an operator. For example, an exemplary auto-configurable simulation system such as any of those described herein may be configured to automatically perform reprogramming operations such as those described herein merely as a result of being communicatively connected (e.g., plugged in) to a computer-assisted surgical system, without requiring additional input from an operator.

An exemplary computer-assisted surgical system with a first type of surgical instrument manipulating system will now be described with reference to FIG. 1. The described exemplary computer-assisted surgical system is illustrative and not limiting. Auto-configurable simulation systems such as those described herein may operate as part of or in conjunction with the described computer-assisted surgical system and/or any other suitable computer-assisted surgical system.

FIG. 1 illustrates an exemplary computer-assisted surgical system 100 ("surgical system 100"). As shown, surgical system 100 may include a surgical instrument manipulating system 102-1 ("manipulating system 102-1"), a user control console 104-1, and an auxiliary system 106 communicatively coupled one to another.

Surgical system 100 may be utilized by a surgical team to perform a computer-assisted surgical procedure on a patient 108. As shown, the surgical team may include a surgeon 110-1, an assistant 110-2, a nurse 110-3, and an anesthesiologist 110-4, all of whom may be collectively referred to as "surgical team members 110," Additional or alternative surgical team members may be present during a surgical session as may serve a particular implementation.

While FIG. 1 illustrates an ongoing minimally invasive surgical procedure, surgical system 100 may similarly be used to perform open surgical procedures or other types of surgical procedures that may similarly benefit from the accuracy and convenience of surgical system 100. Additionally, it will be understood that the surgical session throughout which surgical system 100 may be employed may not only include an operative phase of a surgical procedure, as is illustrated in FIG. 1, but may also include preoperative, postoperative, and/or other suitable phases of the surgical procedure, A surgical procedure may include any procedure in which manual and/or instrumental techniques (e.g., teleoperated instrumental techniques) are used on a patient to investigate, diagnose, or treat a physical condition of the patient. Additionally, a surgical procedure may include any procedure that is not performed on a live patient, such as a calibration procedure, a simulated training procedure, and an experimental or research procedure.

As shown in FIG. 1, surgical instrument manipulating system 102-1 may include a plurality of manipulator arms 112 (e.g., manipulator arms 112-1 through 112-4) to which a plurality of surgical instruments (not shown) may be coupled, Each surgical instrument may be implemented by any suitable surgical tool (e.g., a tool having tissue-interaction functions), medical tool, monitoring instrument (e.g., an imaging device such as an endoscope), sensing instrument (e.g., a force-sensing surgical instrument), diagnostic instrument, or the like that may be used for a computer-assisted surgical procedure (e.g., by being at least partially inserted into patient 108 and manipulated to perform a computer-assisted surgical procedure on patient 108). In the example, shown in FIG. 1, manipulator arms 112 of manipulating system 102-1 are attached on a distal end of an overhead boom that extends horizontally. However, manipulator arms 112 may have other configurations in certain implementations. In addition, while manipulating system 102-1 is depicted and described herein as including four manipulator arms 112, it will be recognized that manipulating system 102-1 may include only a single manipulator arm 112 or any other number of manipulator arms as may serve a particular implementation.

Manipulator arms 112 and/or surgical instruments attached to manipulator arms 112 may include one or more displacement transducers, orientational sensors, and/or positional sensors (hereinafter "surgical system sensors") used to generate raw (e.g., uncorrected) kinematics information. One or more components of surgical system 100 may be configured to use the kinematics information to track (e.g., determine positions of) and/or control the surgical instruments.

In addition, manipulator arms 112 may each include or otherwise be associated with a plurality of motors that control movement of manipulator arms 112 and/or the surgical instruments attached thereto. For example, manipulator arm 112-1 may include or otherwise be associated with a first internal motor (not explicitly shown) configured to yaw manipulator arm 112-1 about a yaw axis. In like manner, manipulator arm 112-1 may be associated with a second internal motor (not explicitly shown) configured to drive and pitch manipulator arm 112-1 about a pitch axis. Likewise, manipulator arm 112-1 may be associated with a third internal motor (not explicitly shown) configured to slide manipulator arm 112-1 along insertion axis. Manipulator arms 112 may each include a drive train system driven by one or more of these motors in order to control the pivoting of manipulator arms 112 in any manner as may serve a particular implementation. As such, if a surgical instrument attached, for example, to manipulator arm 112-1 is to be mechanically moved, one or more of the motors coupled to the drive train may be energized to move manipulator arm 112-1.

In certain examples, manipulator arms 112 may have one or more clutch modes that facilitate manipulator arms 112 being disengaged from one or more of the motors of manipulator arms 112. Manipulator arms 112 may have any suitable number of clutch modes as may serve a particular implementation. For example, a first clutch mode may be engaged to allow manipulator arm 112-1 to manually rotate about a yaw axis, a second clutch mode may be engaged to allow manipulator arm 112-1 to manually rotate about a pitch axis, and a third clutch mode may be engaged to allow manipulator arm 112-1 to manually move along an insertion axis. Any suitable number of the clutch modes may be engaged at a particular time to facilitate a user manually repositioning an insertion trajectory of surgical instruments attached to manipulator arms 112.

Surgical instruments attached to manipulator arms 112 may each be positioned at a surgical space associated with a patient. A "surgical space" may, in certain examples, be entirely disposed within a patient and may include an area within the patient at or near where a surgical procedure is planned to be performed, is being performed, or has been performed. For example, for a minimally invasive surgical procedure being performed on tissue internal to a patient, the surgical space may include the tissue, anatomy underlying the tissue, as well as space around the tissue where, for example, surgical instruments being used to perform the surgical procedure are located. In other examples, a surgical space may be at least partially disposed external to the patient at or near where a surgical procedure is planned to be performed, is being performed, or has been performed on the patient. For instance, surgical system 100 may be used to perform an open surgical procedure such that part of the surgical space (e.g., tissue being operated on) is internal to the patient while another part of the surgical space (e.g., a space around the tissue where one or more surgical instruments may be disposed) is external to the patient. A surgical instrument may be referred to as being positioned or located at or within a surgical space when at least a portion of the surgical instrument (e.g., a distal portion of the surgical instrument) is located within the surgical space.

User control console 104-1 may be configured to facilitate control by surgeon 110-1 of manipulator arms 112 and surgical instruments attached to manipulator arms 112. For example, surgeon 110-1 may interact with user control console 104-1 to remotely move or manipulate manipulator arms 112 and the surgical instruments. To this end, user control console 104-1 may provide surgeon 110-1 with imagery (e.g., high-definition three-dimensional (3D) imagery) of a surgical space associated with patient 108 as captured by an imaging device. In certain examples, user control console 104-1 may include a stereoscopic image viewer having two displays where stereoscopic images (e.g., 3D images) of a surgical space associated with patient 108 and generated by a stereoscopic imaging system may be viewed by surgeon 110-1. Surgeon 110-1 may utilize the imagery to perform one or more procedures with one or more surgical instruments attached to manipulator arms 112.

To facilitate control of surgical instruments, user control console 104-1 may include a set of master controls (not shown). These master controls may be manipulated by surgeon 110-1 to control movement of surgical instruments (e.g., by utilizing robotic and/or teleoperation technology). The master controls may be configured to detect a wide variety of hand, wrist, and finger movements by surgeon 110-1. In this manner, surgeon 110-1 may intuitively perform a surgical procedure using one or more surgical instruments.

User control console 104-1 may further be configured to facilitate control by surgeon 110-1 of other components of surgical system 100. For example, surgeon 110-1 may interact with user control console 104-1 to change a configuration or operating mode of surgical system 100, to change a display mode of surgical system 100, to generate additional control signals used to control surgical instruments attached to manipulator arms 112, to facilitate switching control from one surgical instrument to another, to initiate display of a representation of an insertion trajectory, or to perform any other suitable operation. To this end, user control console 104-1 may also include one or more input devices (e.g., foot pedals, buttons, switches, etc.) configured to receive input from surgeon 110-1.

In certain examples, user control console 104-1 may be reconfigurable or reprogrammable to control different types of surgical instrument manipulating systems (e.g., different models of surgical instrument manipulating systems). As such, user control console 104-1 may include a control system that may include or be implemented by hardware and/or software components (e.g., hardware boards, hardware nodes, software nodes, processors, memories, etc.) that may be reconfigured or reprogramed. In addition, such a control system of user control console 104-1 may include hardware and/or software components configured to run algorithms associated with controlling different types of surgical instrument manipulating systems.

Auxiliary system 106 may include one or more computing devices configured to perform primary processing operations of surgical system 100. The one or more computing devices included in auxiliary system 106 may control and/or coordinate operations performed by various other components (e.g., manipulating system 102-1 and/or user control console 104-1) of surgical system 100. For example, a computing device included in user control console 104-1 may transmit instructions to manipulating system 102-1 by way of the one or more computing devices included in auxiliary system 106. As another example, auxiliary system 106 may receive, from manipulating system 102-1, and process image data representative of imagery captured by an imaging device attached to one of manipulator arms 112.

In some examples, auxiliary system 106 may be configured to present visual content to surgical team members 110 who may not have access to the images provided to surgeon 110-1 at user control console 104-1. To this end, auxiliary system 106 may include a display monitor 114 configured to display one or more user interfaces, such as images (e.g., 2D images) of the surgical space, information associated with patient 108 and/or the surgical procedure, and/or any other visual content as may serve a particular implementation. For example, display monitor 114 may display images of the surgical space together with additional content (e.g., representations of insertion trajectories, graphical content, contextual information, etc.) concurrently displayed with the images. In some embodiments, display monitor 114 is implemented by a touchscreen display with which surgical team members 110 may interact (e.g., by way of touch gestures) to provide user input to surgical system 100.

Manipulating system 102-1, user control console 104-1, and auxiliary system 106 may be communicatively coupled one to another in any suitable manner. For example, as shown in FIG. 1, manipulating system 102-1, user control console 104-1, and auxiliary system 106 may be communicatively coupled by way of control lines 116, which may represent any wired or wireless communication link as may serve a particular implementation. To this end, manipulating system 102-1, user control console 104-1, and auxiliary system 106 may each include one or more wired or wireless communication interfaces, such as one or more local area network interfaces, Wi-Fi network interfaces, cellular interfaces, etc.

Prior to an operator (e.g., surgeon 110-1) using surgical system 100 to perform a surgical procedure, it is desirable to train the operator to use the one or more input devices (e.g., foot pedals, buttons, switches, etc.) of user control console 104-1 to perform one or more procedures and/or to develop certain skillsets associated with using surgical system 100. To that end, surgical system 100 is configured to interface with an auto-configurable simulation system for training purposes. As will be described in more detail herein, auto-configurable simulation systems such as those described herein are configured to both simulate any one of a plurality of surgical instrument manipulating systems and provide a simulated virtual environment for training purposes. Exemplary auto-configurable simulation systems will now be described with reference to FIGS. 2-8.

Figure 2:
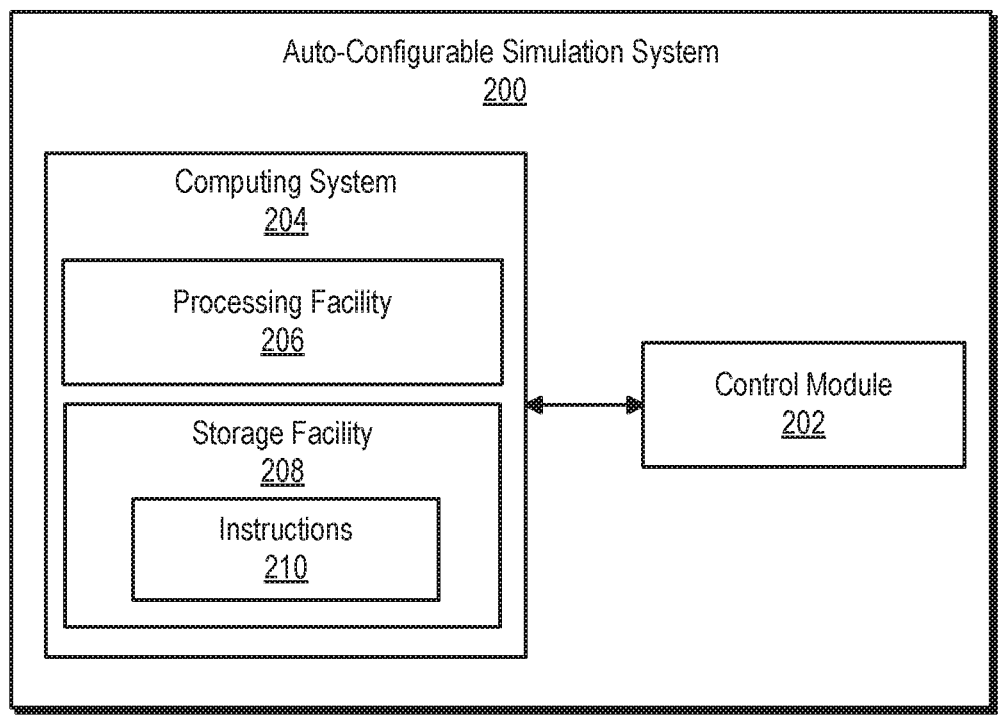
FIG. 2 illustrates an exemplary auto-configurable simulation system according to principles described herein.

FIG. 2 illustrates an exemplary auto-configurable simulation system 200 ("simulation system 200"). As shown, simulation system 200 may include, without limitation, a control module 202 and a computing system 204. Control module 202 is the connection interface through which simulation system 200 communicates with a user control console (e.g., user control console 104-1) and/or any other component (e.g., auxiliary system 106) of a computer-assisted surgical system (e.g., surgical system 100). To that end, control module 202 may include or be implemented by hardware and/or software components (e.g., hardware boards, hardware nodes, software nodes, memories, etc.) to facilitate such communication. In addition, control module 202 may include hardware and/or software components configured to run algorithms associated with simulating different types of surgical instrument manipulating systems. As will be described in more detail herein, the hardware and/or software components of control module 202 and/or the connections between them are configured to be reprogrammable to facilitate control module 202 communicating with the user control console and simulating a surgical instrument manipulating system. Exemplary components that may be included as part of or implemented by control module 202 are described herein.

Computing system 204 includes, without limitation, a processing facility 206 and a storage facility 208 selectively and communicatively coupled to one another. Facilities 206 and 208 may each include or be implemented by hardware and/or software components (e.g., processors, memories, communication interfaces, instructions stored in memory for execution by the processors, etc.). In some examples, facilities 206 and 208 may be distributed between multiple devices and/or multiple locations as may serve a particular implementation.

In certain examples, computing system 204 may include a graphics processing unit ("GPU") that is configured to generate a virtual environment to be presented to an operator during, for example, a virtual surgical training procedure. Alternatively, the processing of the virtual environment may be performed remotely from computing system 204. For example, computing system 204 may receive a streamed virtual environment generated by a cloud-based GPU. Computing system 204 may transmit data representative of a generated or received virtual environment along to a user control console by way of control module 202.

Storage facility 208 may maintain (e.g., store) executable data used by processing facility 206 to perform any of the operations described herein. For example, storage facility 208 may store instructions 210 that may be executed by processing facility 206 to perform any of the operations described herein. Instructions 210 may be implemented by any suitable application, software, code, and/or other executable data instance.

Storage facility 208 may also maintain any data received, generated, managed, used, and/or transmitted by processing facility 206. For example, storage facility 208 may maintain any suitable data associated with a plurality of computer-assisted surgical systems (e.g., configuration parameters, simulation modules, etc.) and/or data associated with generating and/or providing virtual environments for display to an operator of a user control console (e.g., user control console 104-1). In certain examples, storage facility 208 may store firmware associated with each surgical instrument manipulating system included in a plurality of surgical instrument manipulating systems. Such firmware may be used in any suitable manner, such as described herein, to reprogram control module 202 and/or provide a virtual environment for presentation to an operator of a user control console.

Processing facility 206 may be configured to perform (e.g., execute instructions 210 stored in storage facility 208 to perform) various processing operations associated with reprogramming control module 202 and providing virtual environments for display to a user. For example, processing facility 206 may determine, after control module 202 is communicatively coupled to a particular user control console, that the particular user control console is configured to control a different type of surgical instrument manipulating system than control module 202 is currently configured to simulate. Based on such a determination, processing facility 206 may reprogram control module 202 such that control module 202 is configured to simulate the same type of surgical instrument manipulating system that the user control console is configured to control. These and other operations that may be performed by processing facility 206 are described herein.

Simulation system 200 (e.g., processing facility 206) is configured to automatically reprogram control module 202 to simulate any one of a plurality of different types of surgical instrument manipulating systems. To illustrate, FIG. 3 shows an exemplary diagram 300 that depicts simulation system 200 together with a plurality of user control consoles 104 (e.g., user control consoles 104-1 through 104-N) that are each in turn configured to control a respective one of a plurality of surgical instrument manipulating systems 102 (e.g., surgical instrument manipulating systems 102-1 through 102-N).

Figure 3:
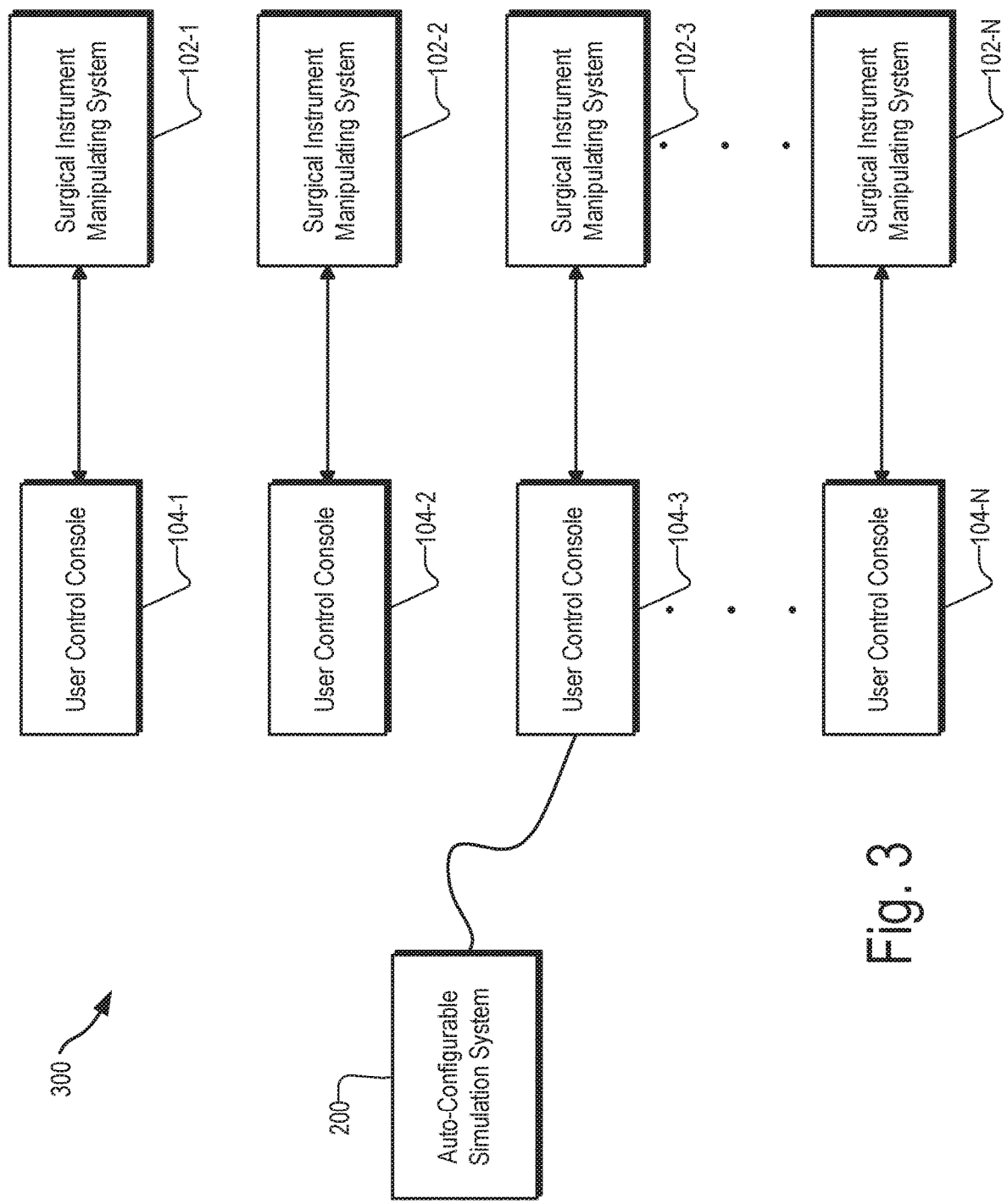
FIG. 3 illustrates an exemplary implementation of an auto-configurable simulation system according to principles described herein.

Although FIG. 3 shows simulation system 200 as being connected to user control console 104-3, it is understood that simulation system 200 may communicatively connect to any other suitable component associated with a computer-assisted surgical system to facilitate automatically reprogramming control module 202. For example, simulation system 200 may communicatively connect to an auxiliary system (e.g., an auxiliary system similar to auxiliary system 106) associated with surgical instrument manipulating system 102-3 instead of user control console 104-3 in certain examples. Simulation system 200 may then automatically reprogram control module 202 in any suitable manner, such as described herein, based on information received from the auxiliary system.

Each surgical instrument manipulating system 102 may correspond to a different type of surgical instrument manipulating system having a different configuration. For example, a first type of surgical instrument manipulating system may have a first manipulator arm configuration, and second type of surgical instrument manipulating system may have a second manipulator arm configuration. The first manipulator arm configuration may be different from the second manipulator arm configuration. To illustrate, surgical instrument manipulating system 102-1 may have a manipulator arm configuration where the manipulator arms (e.g., manipulator arms 112) are attached to a distal end of a horizontally extendable overhead boom (such as is shown in FIG. 1). On the other hand, surgical instrument manipulating system 102-2 may have a manipulator arm configuration where there is only one manipulator arm that has a plurality of surgical instruments attached thereto.

The differences between the various types of surgical instrument manipulating systems included in plurality of surgical instrument manipulating systems 102 may require different communication interfaces and/or employ different algorithms to operate. This in turn may result in simulation system 200 not being able to fully communicate with certain user control consoles 104. For example, control module 202 of simulation system 200 may be currently programmed to simulate surgical instrument manipulating system 102-1, As such, when simulation system 200 is communicatively connected to user control console 104-1, simulation system 200 is able to communicate with and interact with user control console 104-1 as though it was surgical instrument manipulating system 102-1 (i.e., to simulate surgical instrument manipulating system 102-1). However, if simulation system 200 is subsequently communicatively connected to user control console 104-2, one or more communication components (e.g., hardware nodes, software nodes, etc.) of control module 202 may not be programmed to simulate surgical instrument manipulating system 102-2. As a result, user control console 102-2 may limit communication with simulation system 200 as control module 202 is currently configured.

To facilitate simulation system 200 communicating with a different user control console (e.g., user control console 102-2) and/or some other component of a computer-assisted surgical system, system 200 may first determine whether control module 202 is currently configured to simulate the type of surgical instrument manipulating system that the particular user control console is configured to control. In certain examples, simulation system 200 may determine whether control module 202 is currently configured to simulate a given surgical instrument manipulating system 102 upon being communicatively connected to a corresponding user control console 104.

Figure 4:
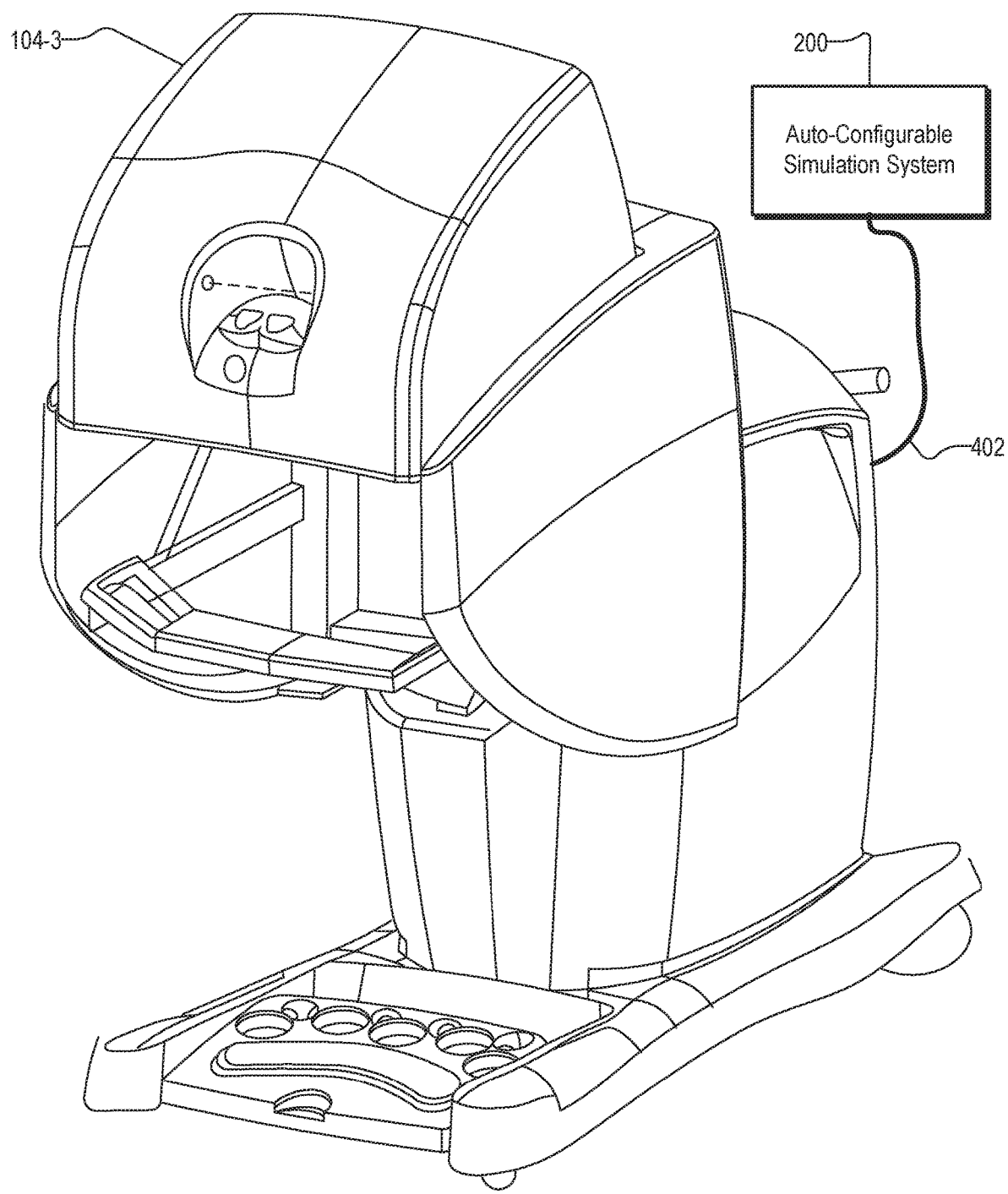
FIG. 4 illustrates an exemplary user control console according to principles described herein.

Simulation system 200 may communicatively connect to a user control console in any suitable manner. For example, simulation system 200 may communicatively connect to a user control console through any suitable wired or wireless communication link. In the example shown in FIG. 3, simulation system 200 is communicatively connected to user control console 104-3, FIG. 4 shows an example where simulation system 200 is communicatively connected to user control console 104-3 by way of a wired communication link 402, which may be a high bandwidth fiber optic communication link or any other suitable wired communication link. In certain examples, wired communication link 402 may connect to the same connection interface of user control console 104-3 as would an additional wired communication link that would otherwise extend from surgical instrument manipulating system 102-3 to user control console 104-3 during normal operation of a surgical system that includes surgical instrument manipulating system 102-3 to user control console 104-3.

Regardless of which type of communication link is used to communicatively connect simulation system 200 to a user control console, it is understood that the user control console interacts with simulation system 200 as though simulation system 200 was the corresponding surgical instrument manipulating system, That is, the user control console sends and receives communication signals the same as when the user control console is communicating with a certain type of surgical instrument manipulating system by way of such a communication link.

When simulation system 200 is communicatively connected to a user control console, simulation system 200 may determine that control module 202 is configured to simulate a type of surgical instrument manipulating system that is different from the surgical instrument manipulating system that the user control console is configured to control. For example, in the example shown in FIG. 4, after simulation system 200 communicatively connects with user control console 104-3, simulation system 200 may receive a handshake signal from user control console 104-3. The handshake signal may include data identifying surgical instrument manipulating system 102-3 as the type of surgical instrument manipulating system that user control console 104-3 is configured to control, Simulation system 200 may then compare the data from the handshake signal with the current configuration of control module 202 to determine whether control module is currently configured to simulate surgical instrument manipulating system 102-3 or some other type of surgical instrument manipulating system.

Figure 5:
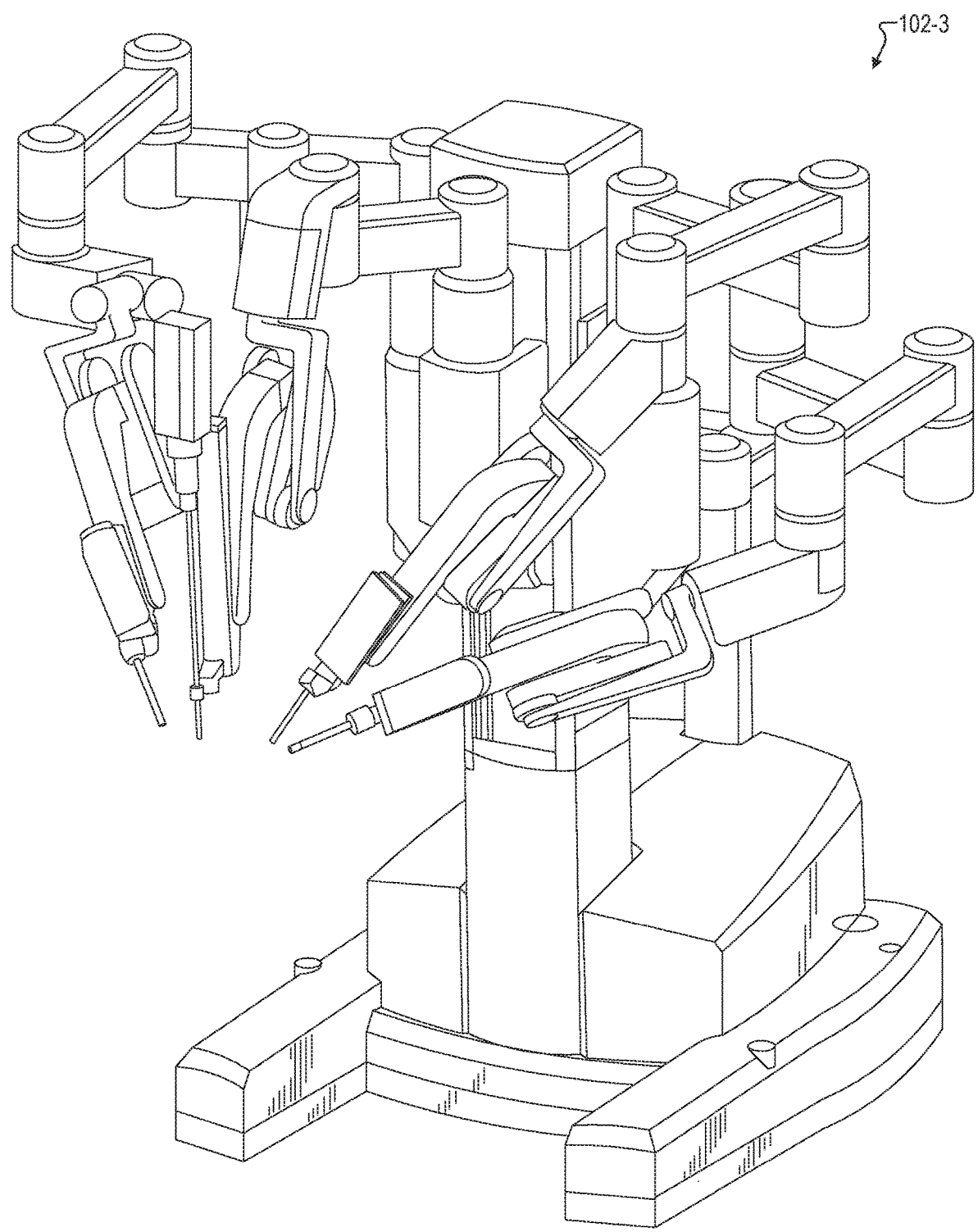
FIG. 5 illustrates an exemplary surgical instrument manipulating system according to principles described herein.

If control module 202 is already currently configured to simulate surgical instrument manipulating system 102-3, then simulation system 200 may communicate with user control console 104-3 in any suitable manner without reprogramming control module 202, However, if control module 202 is currently configured to simulate a different type of surgical instrument manipulating system, simulation system 200 may reprogram control module 202 in any suitable manner, such as described herein. To illustrate an example, control module 202 may be currently configured to simulate surgical instrument manipulating system 102-1 shown in FIG. 1. However, as shown in FIG. 4, simulation system 200 is currently communicatively connected to user control console 104-3, which is configured to control surgical instrument manipulating system 102-3. Surgical instrument manipulating system 102-3 may be a different type of surgical instrument manipulating system than surgical instrument manipulating system 102-1. For example, as shown in FIG. 5, surgical instrument manipulating system 102-3 may include a plurality of manipulator arms connected to a vertically extending pillar, whereas surgical instrument manipulating system 102-1 may include a plurality of manipulator arms attached to a horizontally extendable overhead boom. Additional differences between surgical instrument manipulating systems of different types may include different types of surgical instruments, different numbers of imaging devices (e.g., endoscopes), and/or different algorithms used to control the associated manipulator arms. Additionally or alternatively, user control console 104-3 may include different input devices than user control console 104-1. In view of any these differences, the communication components (e.g., hardware nodes and/or software nodes) associated with control module 202 may be reprogrammed to facilitate communication between user control console 104-3 and simulation system 200.

Simulation system 200 may reprogram control module 202 in any suitable manner. For example, simulation system 200 may access, from a plurality of sets of configuration parameters, a set of configuration parameters associated with a particular type of surgical instrument manipulating system. Simulation system 200 may use the set of configuration parameters associated with the particular type of surgical instrument manipulating system to configure control module 202 to communicate with the user control console and execute the algorithms used to control the particular type of surgical instrument manipulating system. In certain examples, simulation system 200 may use such configuration parameters to change the connection components/interfaces (e.g., the connections between nodes/boards, the number of nodes/boards, and/or the configuration of nodes/boards) included in control module 202 such that they match or are at least substantially similar to connection components/interfaces of a particular type of surgical instrument manipulating system. In so doing, simulation system 200 is then configured to interact with a user control console by way of control module 202 as though simulation system 200 is, from the perspective of the user control console, the surgical instrument manipulating system.

In certain examples, the reprogramming of control module 202 may include simulation system 200 erasing firmware stored in embedded memory of control module 202 and replacing the firmware with additional firmware associated with a different type of surgical instrument manipulating system. Continuing with the example described above with reference to FIGS. 4-5, simulation system 200 may delete firmware for surgical instrument manipulating system 102-1 stored in embedded memory of control module 202 and replace that firmware with firmware for surgical instrument manipulating system 102-3. In certain examples, the firmware used to reprogram control module 202 may be retrieved from a memory associated with storage facility 208. Additionally or alternatively, the firmware may be retrieved from any other suitable storage location.

In certain examples, prior to simulation system 200 reprogramming control module 202, simulation system 200 may store data indicating that a user control console is configured to facilitate control of a particular type of surgical instrument manipulating system. Simulation system 200 may store such data in any suitable manner and in any suitable storage device. For example, simulation system 200 may store such data in a memory associated with storage facility 208. After simulation system 200 stores the data indicating the type of surgical instrument manipulating system, simulation system 200 may reprogram control module 202 such that control module 202 is configured to simulate a different type of surgical instrument manipulating system.

In certain examples, simulation system 200 may communicatively disconnect control module 202 from a user control console prior to reprogramming control module 202. Simulation system 200 may communicatively disconnect control module 202 from the user control console in any suitable manner and at any suitable time. In certain examples, simulation system 200 may disconnect control module from the user control console after storing the data indicating the user control console is configured to facilitate control of a different type of surgical instrument manipulating system. In certain examples, simulation system 200 may include either a hardware switch or a software switch that temporarily severs a communication link between control module 202 and the user control console. By communicatively disconnecting control module 202 from the user control console, it may be possible to prevent simulation system 200 from inadvertently reprogramming the control system of the user control console in addition to reprogramming control module 202. After simulation system 200 reprograms control module 202, simulation system 200 may communicatively reconnect control module 202 to the user control console, such as by restoring the severed communication link or establishing a new communication link between control module 202 and the user control console.

In certain examples, simulation system 200 may provide one or more notifications configured to alert an operator of a user control console that simulation system 200 is performing a reprogramming operation. Such a notification may include any suitable information and may be provided to the operator in any suitable manner. For example, such a notification may be provided to the operator by way of a display device associated with a user control console. In certain examples, simulation system 200 may provide such a notification upon initiation of the reprogramming operation. Additionally or alternatively, simulation system 200 may provide one or more additional notifications during the reprogramming operation. For example, an additional notification may include information indicating a time to completion associated with the reprogramming operation.

Figure 6:
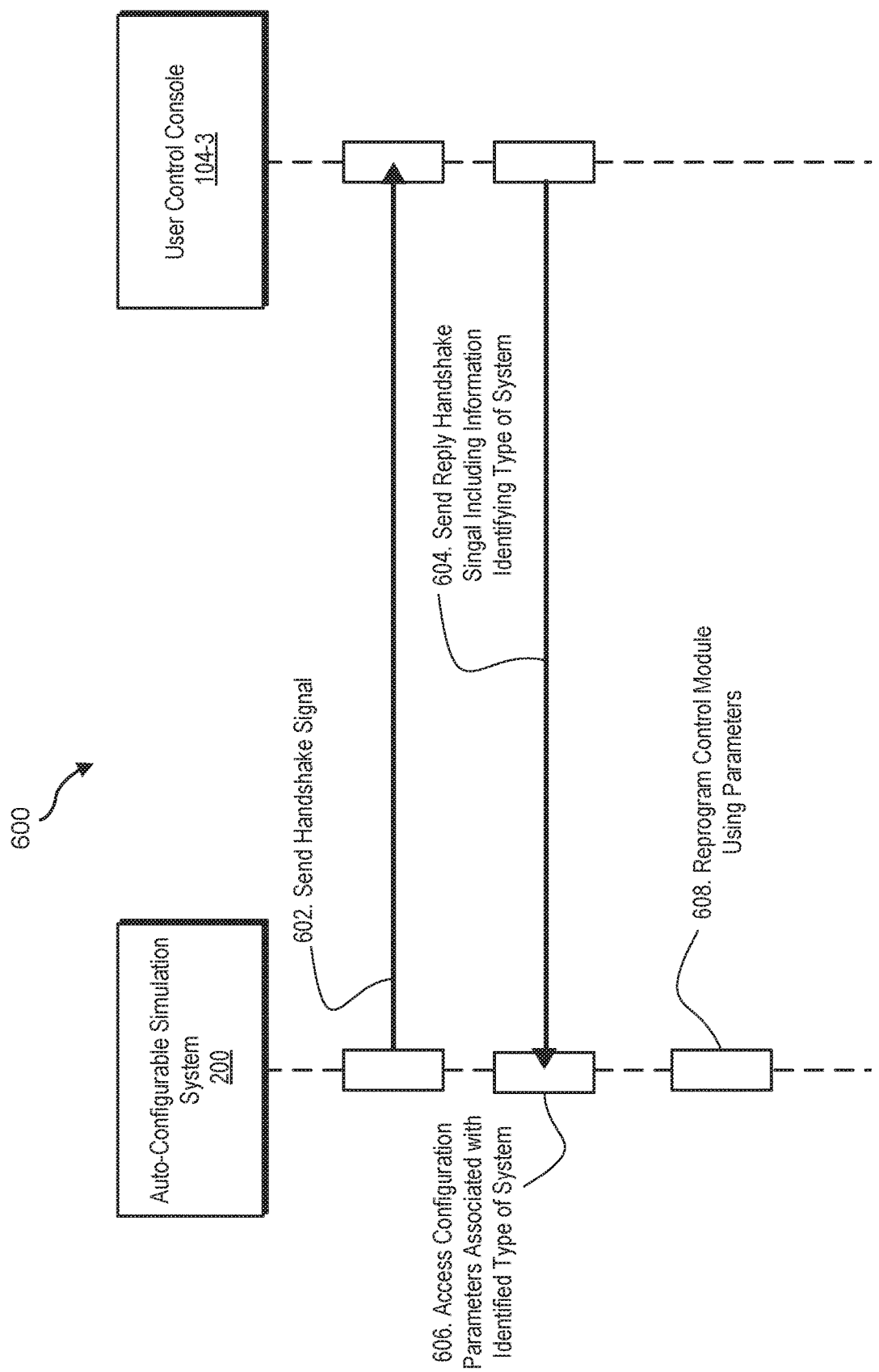
FIG. 6 illustrates an exemplary sequence diagram according to principles described herein.

FIG. 6 illustrates an exemplary sequence diagram 600 showing communications that may occur between simulation system 200 and user control console 104-3 in certain implementations. As shown in FIG. 6, after control module 202 communicatively connects to user control console 104-3, simulation system 200 may send a handshake signal in operation 602. In response to the handshake signal, user control console 104-3 may send a reply handshake signal in operation 604. The reply handshake signal includes at least information identifying the type of surgical instrument manipulating system (e.g., surgical instrument manipulating system 102-3) that user control console 104-3 is configured to control and/or any other suitable information associated with user control console 104-3. Based on the information identifying the type of surgical instrument manipulating system, simulation system 200 may access a set of configuration parameters associated with the identified type of surgical instrument manipulating system in operation 606. Simulation system 200 may then use the set of configuration parameters to reprogram, in operation 608, control module 202 such that control module 202 is configured to simulate the type of surgical instrument manipulating system identified in the information provided in operation 604.

Simulation system 200 may repeat operations such as those described herein to facilitate simulating different types of surgical instrument manipulating systems. To illustrate, after simulation system 200 reprograms control module 202 and after simulation system 200 disconnects from user control console 104-3, simulation system 200 may communicatively connect to an additional user control console (e.g., user control console 104-2). Simulation system 200 may determine that the additional user control console is configured to control a different type of surgical instrument manipulating system than surgical instrument manipulating system 102-3. In response to such a determination, simulation system 200 may reprogram control module 202 again to be configured to simulate the additional type of surgical instrument manipulating system instead of surgical instrument manipulating system 102-3. If simulation system 200 is subsequently reconnected to user control console 104-3, simulation system 200 may reprogram control module 202 again to simulate surgical instrument manipulating system 102-3 instead of the additional type of surgical instrument manipulating system.

Figure 7:
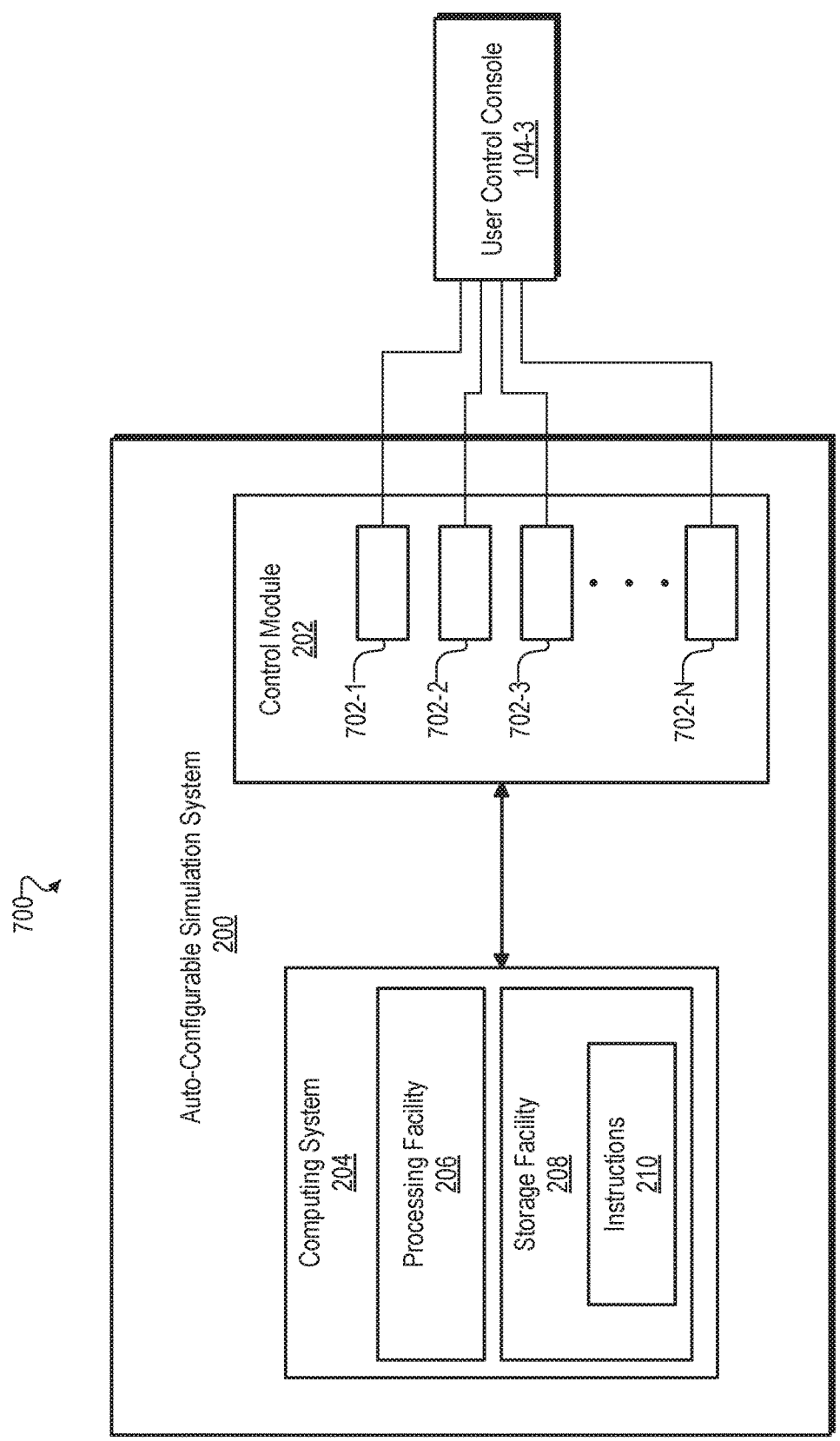
FIGS. 7-8 illustrate exemplary implementations of an auto-configurable simulation system according to principles described herein.

In certain examples, control module 202 may include a plurality of hardware boards that each correspond to a different component of a computer-assisted surgical system (e.g., computer-assisted surgical system 100). To illustrate, FIG. 7 shows an exemplary implementation 700 in which control module 202 includes a plurality of hardware boards 702 (e.g., boards 702-1 through 702-N). For example, board 702-1 may correspond to a hardware board included in surgical instrument manipulating system 102-1, board 702-2 may correspond to a hardware board included auxiliary system 106, etc. Boards 702 may each include hardware nodes, software nodes, or some combination thereof configured to facilitate communication with a user control console (e.g., user control console 104-1). In certain examples, each of hardware boards 702 may include a plurality of nodes corresponding to different components of a surgical instrument manipulating system. For example, board 702-1 may include a first node corresponding to a first manipulator arm, a second node corresponding to a second manipulator arm, a third node corresponding to a third manipulator arm, etc. of surgical instrument manipulating system 102-1. Simulation system 200 may be configured to reprogram boards 702 in any suitable manner, such as described herein, such that the nodes of boards 702 are configured to facilitate communication with another user control console (e.g., user control console 104-3) and simulate another surgical instrument manipulating system (e.g., surgical instrument manipulating system 102-3).

Figure 8:
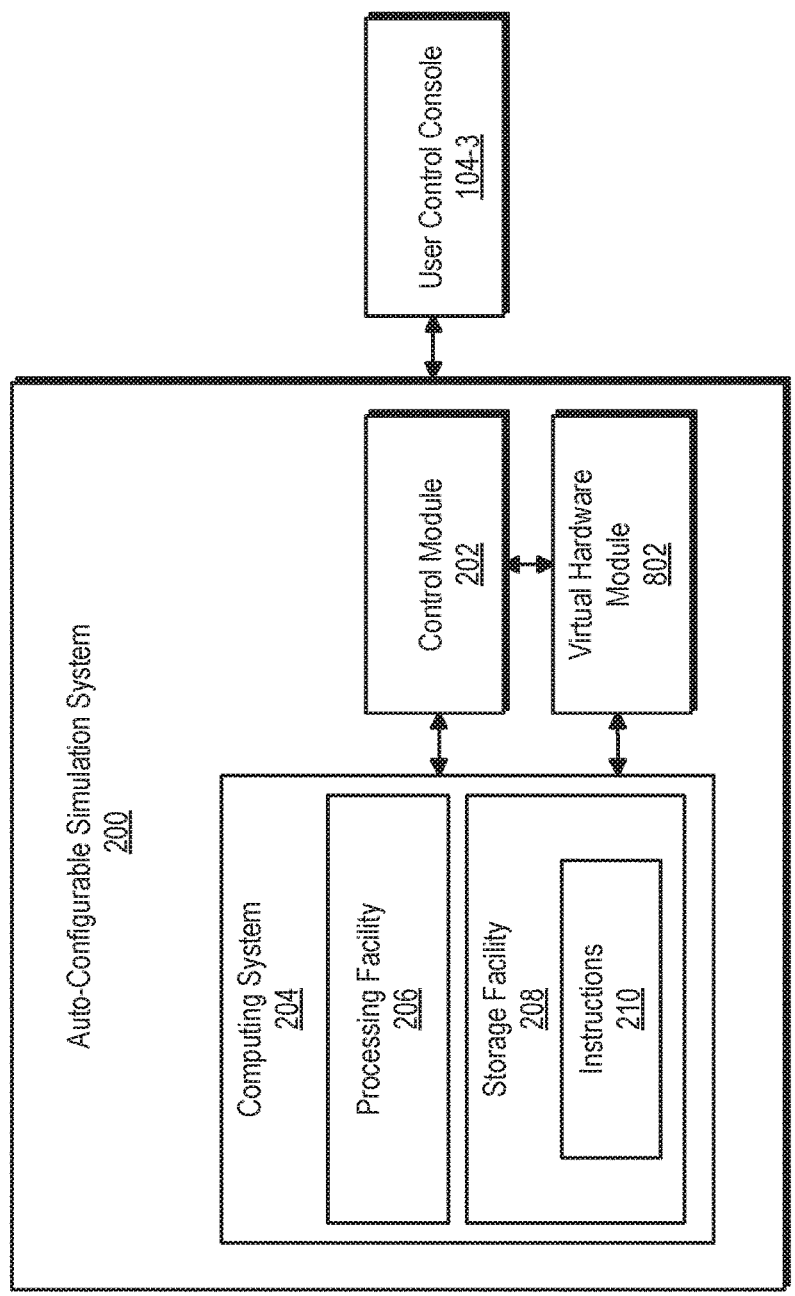

In certain examples, simulation system 200 may reprogram a virtual hardware module to simulate a component of a particular type of surgical instrument manipulating system. Such a virtual hardware module may be implemented in any suitable manner. For example, FIG. 8 shows an exemplary implementation 800 in which simulation system 200 includes or otherwise implements a virtual hardware module 802. In certain examples, virtual hardware module 802 may be implemented by or included as part of computing system 204. Alternatively, virtual hardware module 802 may be located remotely from computing system 204 (e.g., on a cloud server).

By reprogramming a virtual hardware module such as virtual hardware module 802, it may be possible to significantly reduce the amount of time that may be required to reprogram control module 202 to simulate a surgical instrument manipulating system. This is because reprogramming the hardware components of control module 202 may, in certain examples, include erasing and rewriting embedded memory of control module 202, which may be relatively time consuming. To facilitate reprogramming control module 202 more quickly, simulation system 200 may detect that control module 202 is communicatively connected to, for example, user control console 104-3. After simulation system 200 determines that user control console 104-3 is configured to control surgical instrument manipulating system 102-3, simulation system 200 may reprogram virtual hardware module 802 so as to run a virtual machine that virtualizes one or more of the hardware components (e.g., boards, nodes, etc.) that would otherwise be included as part of control module 202. It is understood that, when simulation system 200 reprograms a virtual hardware module, simulation system 200 may also automatically reprogram one or more connection interfaces of control module 202 such that control module 202 is able to communicate sufficiently with user control console 104-3.

In certain examples, simulation system 200 may be configured to provide different graphical user interfaces for display to a user depending on which type of surgical instrument manipulating system control module 202 is currently configured to simulate. For example, simulation system 200 may provide a first set of graphical user interfaces for display to a user if control module 202 is configured to simulate a first type of surgical instrument manipulating system and may provide a second set of graphical user interfaces for display to a user if control module 202 is configured to simulate a second type of surgical instrument manipulating system. In certain examples, simulation system 200 may change the graphical user interface based on the type of surgical instrument that is currently being used as part of a simulated procedure.

Figure 9:
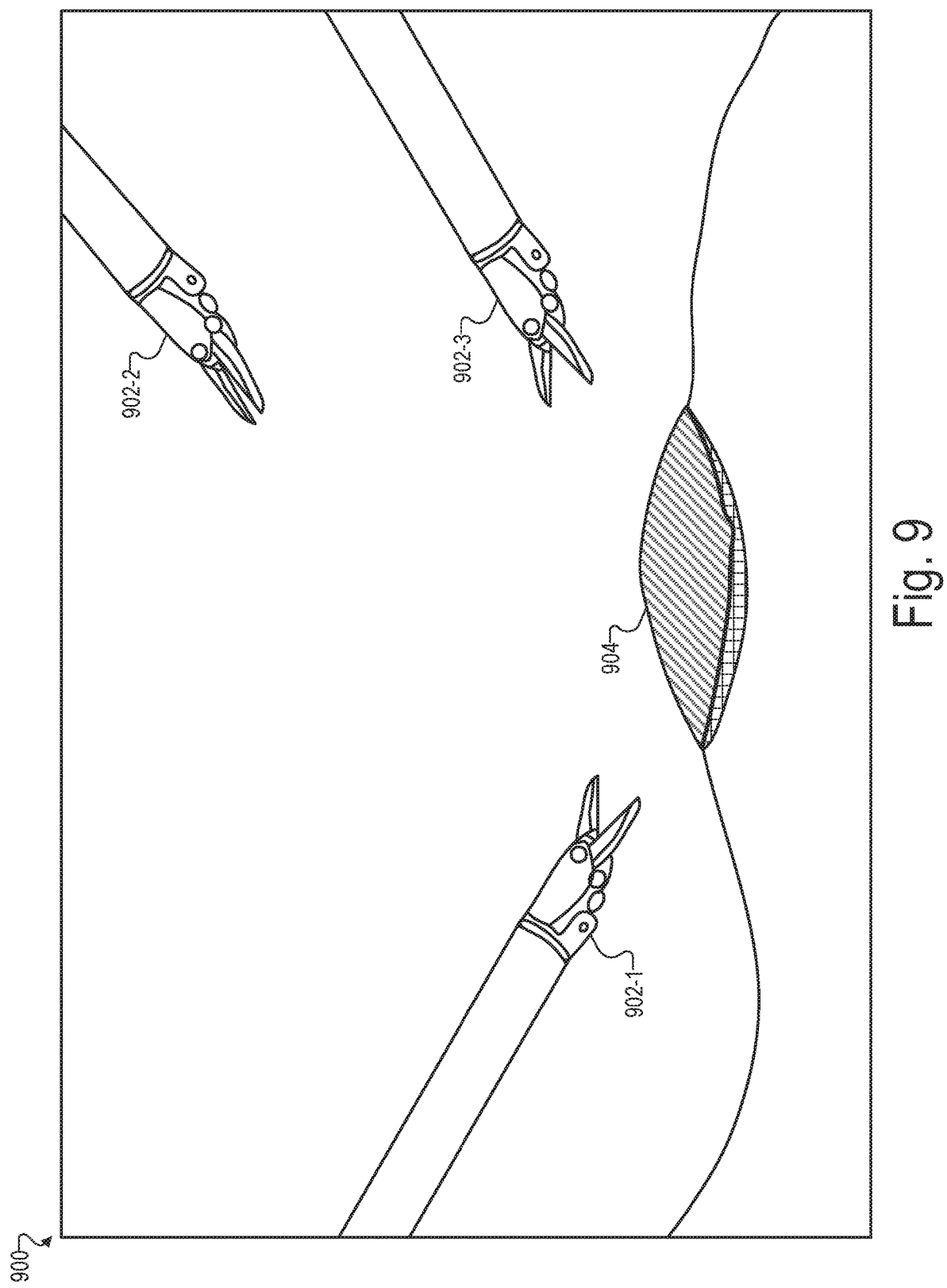
FIG. 9 illustrates an exemplary virtual environment that may be provided for display by a display device of a user control console according to principles described herein.

After simulation system 200 reprograms control module 202, simulation system 200 may provide a virtual environment for display by a display device of a user control console. With such a virtual environment, simulation system 200 is configured to provide an operator with the exact same experience as would be provided if the operator were controlling the actual surgical instrument manipulating system. Such a virtual environment may include any suitable content to facilitate training an operator to operate a user control console and/or perform a simulated procedure. For example, the virtual environment may include one or more virtual instruments that are movable in response to movement of an input device of a user control console for performing the simulated procedure, To illustrate, FIG. 9 shows an exemplary virtual environment 900 that may be provided for display by simulation system 200. As shown in FIG. 9, virtual environment 900 includes a plurality of virtual surgical instruments 902 (e.g., virtual surgical instruments 902-1 through 902-3) that are depicted in relation to a virtual work site 904. Although FIG. 9 shows three virtual surgical instruments 902, it is understood that any number and/or type of virtual surgical instruments may be depicted within a virtual environment as may serve a particular implementation. Virtual environment 900 may include any suitable additional or alternative instrument or device, such as those described herein, as may serve a particular implementation. For example, virtual environment 900 may include one or more virtual imaging devices such as a virtual endoscope in certain implementations. Additionally or alternatively, virtual environment 900 may include any suitable graphic, icon, training aid, etc. as may serve a particular implementation.

In certain examples, a virtual environment may be generated based on configuration parameters associated with a particular type of surgical instrument manipulating system. As such, the virtual environment may be specific to a particular type of surgical instrument manipulating system and/or type of surgical instrument used as part of the particular type of surgical instrument manipulating system. For example, the angles of insertion, port placement, depth of insertion, number, and/or types of virtual surgical instruments shown in a virtual environment (e.g., virtual environment 900) may be unique to a particular type of surgical instrument manipulating system (e.g., surgical instrument manipulating system 102-1). As such, the appearance of the virtual environment may change depending on which type of surgical instrument manipulating system control module 202 is configured to simulate.

In certain examples, the virtual environment may change depending on the number of ports associated with the surgical instrument manipulating system being simulated. For example, a surgical instrument manipulating system that utilizes a single port may be associated with a different virtual environment than a surgical instrument manipulating system that utilizes multiple ports.

Additionally or alternatively, a virtual work site (e.g., virtual work site 904) may be indicative of a specific surgical location operated on by a particular type of surgical instrument manipulating system. In certain examples, simulation system 200 may be configured to provide any number of different virtual environments depending on the type of surgical instrument manipulating system currently being simulated.

In certain examples, simulation system 200 may implement a single simulation module that may be used to provide a virtual environment associated with any one of a plurality of types surgical instrument manipulating systems. In such examples, simulation system 200 may configure the single simulation module by loading configuration parameters associated with a particular surgical instrument manipulating system prior to providing a virtual environment associated with the particular surgical instrument manipulating system to a user control console. If simulation system 200 is subsequently reprogrammed to simulate a different type of surgical instrument manipulating system, the loaded configuration parameters may then be exchanged for additional configuration parameters associated with the different type of surgical instrument manipulating system.

In certain examples, simulation system 200 may provide a simulator interface through which virtual environments are selectable by an operator (e.g., a trainee) of a user control console. The simulator interface may be a standalone unit (e.g., a laptop computer, a tablet, etc.) with its own monitor or it may be part of the user control console. The virtual environment may be selected through one or more menus provided for display by the simulator interface. For example, the operator may select a virtual procedure icon in a menu to initiate a virtual suturing procedure to develop dexterity in manipulating surgical instruments to perform basic suturing exercises.

After the operator selects a virtual procedure icon, simulation system 200 may access data usable to generate the virtual environment associated with the virtual procedure. In certain examples, such data may be stored by storage facility 208. Additionally or alternatively, such data may be stored remotely from computing system 204. The data may include information indicating which surgical instruments will be used to perform the virtual procedure and three-dimensional objects data for a virtual work site (e.g., virtual work site 904) associated with the virtual procedure.

In certain examples, simulation system 200 may be a computer model of a surgical instrument manipulating system (e.g., surgical instrument manipulating system 102-1). Simulation system 200 simulates movement of surgical instruments in response to movement of operatively associated input devices (e.g., master controls, foot pedals, buttons, switches, etc.) of a user control console by utilizing computer models of components of the surgical instrument manipulating system. As such, commands transmitted to simulation system 200 from the user control console are identical to those that would be transmitted to the actual surgical instrument manipulating system. In particular, the commands to move a manipulator arm that would normally be transmitted to the surgical instrument manipulating system would be transmitted instead to simulation system 200 as input to its computer modeled manipulator arm and associated virtual surgical instrument (e.g., virtual surgical instrument 902-1).

The virtual procedure selected by the operator through the simulator interface defines a virtual environment including information of objects that the operator is to virtually interact with by controlling the virtual instruments while performing the selected virtual procedure. In order to perform the virtual procedure, information of three-dimensional shapes of the objects at the virtual work site and their positions and orientations relative to a fixed reference frame may be stored by storage facility 208. The objects may be computer generated objects useful for developing skillsets or the objects may be based upon real anatomical structures whose shapes and sizes have been determined using techniques such as Magnetic Resonance Imaging ("MRI"), Computed Tomography ("CT") scanning, Ultrasound imaging, and Stereoscopic imaging.

After simulation system 200 receives the commands from the user control console, simulation system 200 updates, as an example, the positions and orientations of the virtual surgical instruments by applying commanded joint positions to previously determined joint positions of manipulator arms. The positions and orientations of the virtual surgical instruments are determined relative to the same fixed reference of the virtual work site so that they may be registered with objects in the virtual work site. Thus, simulation system 200 continually updates the positions and orientations of the virtual surgical instruments while the operator is performing the virtual procedure and generates three-dimensional views of the virtual instruments and objects of the virtual work site from the perspective of a virtual imaging device which is viewing the virtual work site from a position and orientation in the fixed reference frame. Stereo views of the virtual work site may be generated from stereoscopic views and provided by simulation system 200 to the user control console, so that the computer-generated images may be processed in the same manner as captured images from an actual imaging device attached to the actual surgical instrument manipulating system. Simulation system 200 is configured to provide the generated image information to the user control console, in any suitable manner, so that the generated images may be displayed by way of a display device of the user control console. If the virtual surgical instruments come into contact with virtual objects in the virtual work site, force feedback indicative of such contact may be fed back to the user control console in any suitable manner.

In addition to information of the virtual environment, certain performance measurement criteria and data may be stored by storage facility 208. For example, as the operator repeatedly practices a virtual procedure, various parameter values indicative of the operator's performance may be calculated according to the measurement criteria and stored by storage facility 208, The parameter values may subsequently be presented to the operator on any suitable display screen and in any suitable manner. Histograms or other charts indicating the operator's progress may also be provided. In this way, it is possible to monitor and apprise the operator of increased proficiency in performing a virtual surgical procedure.

Additionally or alternatively, simulation system 200 may use such performance measurement criteria and data to develop performance metrics associated with each virtual procedure. Such performance metrics may be indicative of best practices that may be used to perform virtual surgical procedures. For example, a performance metric may indicate that repositioning a field of view of a virtual endoscope to a specific location results in performing a particular virtual procedure more efficiently. Additionally or alternatively, another performance metric may indicate that orienting a surgical instrument at a certain angle facilitates, for example, performing a suturing procedure proficiently. Such performance metrics may be used in any suitable manner. For example, simulation system 200 may use such performance metrics to inform other operators of best practices associated with a given surgical procedure and/or teach the other operators how to improve efficiency with the surgical procedure.

In certain examples, simulation system 200 may be configured to automatically reprogram itself to simulate a particular type of surgical instrument manipulating system prior to simulation system 200 being communicatively connected to a corresponding user control console. For example, simulation system 200 may receive, in any suitable manner, a notification that instructs simulation system 200 to automatically reprogram control module 202 based on information indicating that simulation system 200 will be used together with a particular user control console in the near future. Based on the notification, simulation system 200 may automatically reprogram control module 202 prior to simulation system 200 being connected to the particular user control console. In such examples, when an operator communicatively connects (e.g., plugs in) simulation system 200 to the user control console, simulation system 200 is already configured to simulate the type of surgical instrument manipulating system that the user control console is configured to control.

Figure 10:
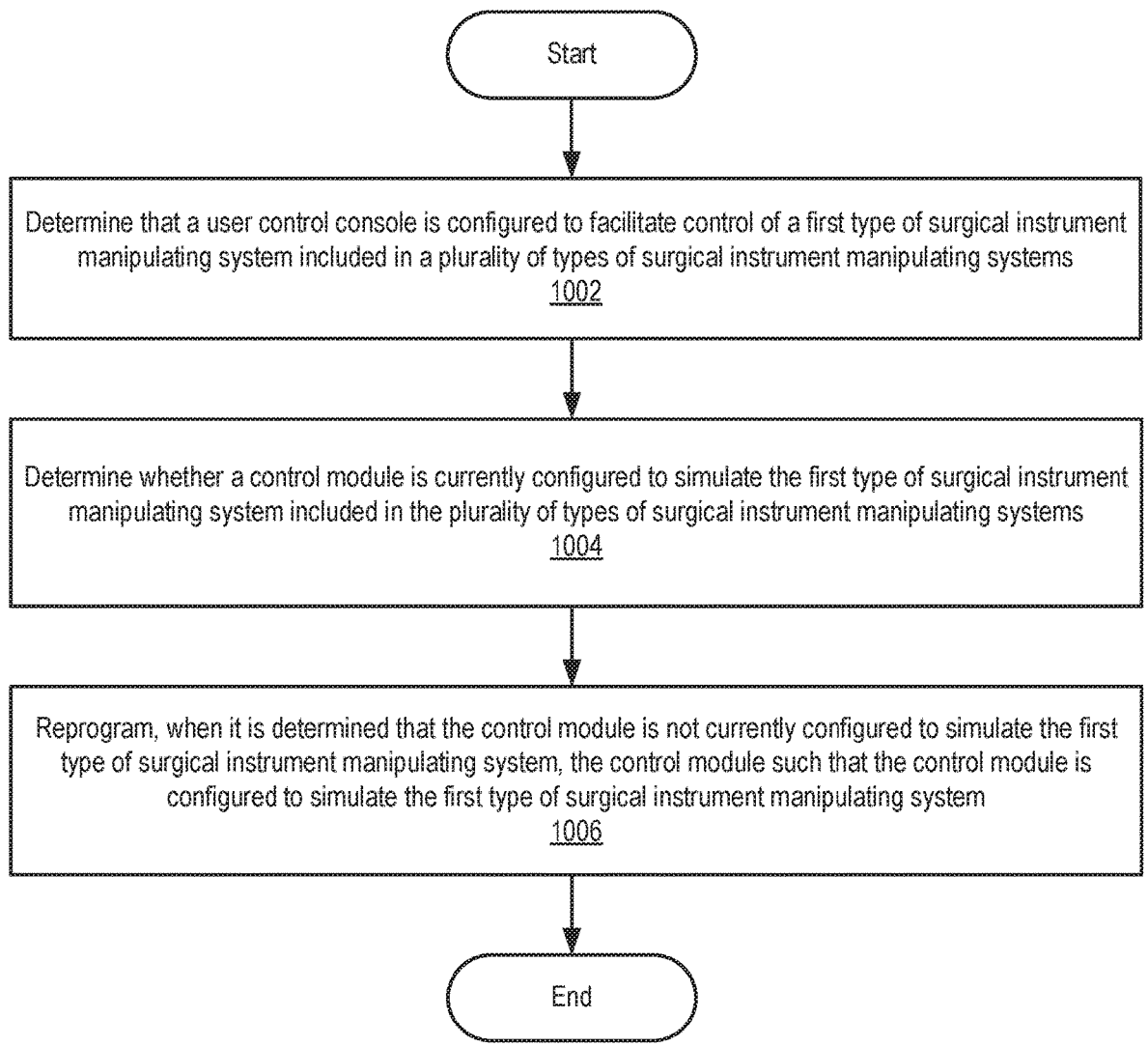
FIGS. 10-11 illustrate exemplary methods according to principles described herein.

FIG. 10 illustrates an exemplary auto-configurable simulation method. While FIG. 10 illustrates exemplary operations according to one embodiment, other embodiments may omit, add to, reorder, and/or modify any of the operations shown in FIG. 10. One or more of the operations shown in FIG. 10 may be performed by a system such as simulation system 200, any components included therein, and/or any implementation thereof.

In operation 1002, a system (e.g., simulation system 200) may determine that a user control console is configured to facilitate control of a first type of surgical instrument manipulating system included in a plurality of types of surgical instrument manipulating systems. As described herein, such a determination may occur after a control module configurable to simulate one of the plurality of types of surgical instrument manipulating systems is communicatively connected to the user control console. Operation 1002 may be performed in any of the ways described herein.

In operation 1004, the system may determine whether the control module is currently configured to simulate the first type of surgical instrument manipulating system included in the plurality of types of surgical instrument manipulating systems, Operation 1004 may be performed in any of the ways described herein.

In operation 1006, when it is determined that the control module is not currently configured to simulate the first type of surgical instrument manipulating system, the system may reprogram the control module such that the control module is configured to simulate the first type of surgical instrument manipulating system. Operation 1006 may be performed in any of the ways described herein.

Figure 11:
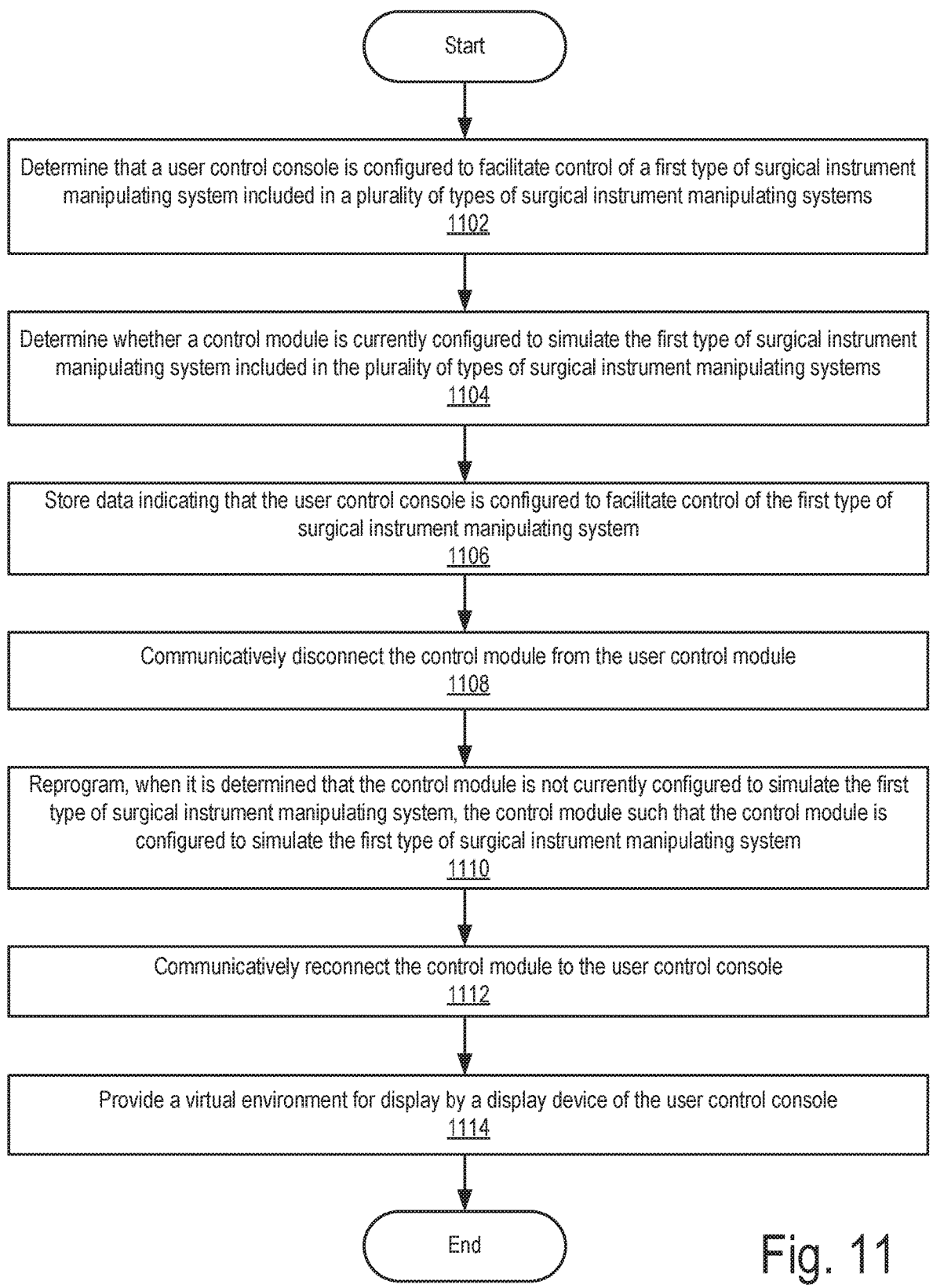

FIG. 11 illustrates another exemplary auto-configurable simulation method. While FIG. 11 illustrates exemplary operations according to one embodiment, other embodiments may omit, add to, reorder, and/or modify any of the operations shown in FIG. 11. One or more of the operations shown in FIG. 11 may be performed by a system such as simulation system 200, any components included therein, and/or any implementation thereof.

In operation 1102, a system (e.g., simulation system 200) may determine that a user control console is configured to facilitate control of a first type of surgical instrument manipulating system included in a plurality of types of surgical instrument manipulating systems. As described herein, such a determination may occur after a control module configurable to simulate one of the plurality of types of surgical instrument manipulating systems is communicatively connected to the user control console. Operation 1102 may be performed in any of the ways described herein.

In operation 1104, the system may determine whether the control module is currently configured to simulate the first type of surgical instrument manipulating system included in the plurality of types of surgical instrument manipulating systems. Operation 1104 may be performed in any of the ways described herein.

In operation 1106, the system may store data indicating that the user control console is configured to facilitate control of the first type of surgical instrument manipulating system. In certain examples, the system may store the data indicating that the user control console is configured to facilitate control of the first type of surgical instrument manipulating system when the system determines that the control module is not currently configured to simulate the first type of surgical instrument manipulating system. Alternatively, the system may be configured to store such data regardless of whether the control module is currently configured to simulate the first type of surgical instrument manipulating system. Operation 1106 may be performed in any of the ways described herein.

In operation 1108, the system may communicatively disconnect the control module from the user control console. In certain examples, the system may perform operation 1108 after storing the data in operation 1106 and in response to the system determining that the control module is not currently configured to simulate the first type of surgical instrument manipulating system. Operation 1108 may be performed in any of the ways described herein.

In operation 1110, when it is determined that the control module is not currently configured to simulate the first type of surgical instrument manipulating system, the system may reprogram the control module such that the control module is configured to simulate the first type of surgical instrument manipulating system. Operation 1110 may be performed in any of the ways described herein.

In operation 1112, the system may, after reprogramming the control module, communicatively reconnect the control module to the user control console. Operation 1112 may be performed in any of the ways described herein.

In operation 1114, the system may provide a virtual environment for display by a display device of the user control console. As described herein, the virtual environment may include a virtual instrument that is movable in response to movement of an input device of the user control console for performing a simulated procedure in the virtual environment, Operation 1114 may be performed in any of the ways described herein.

In some examples, a non-transitory computer-readable medium storing computer-readable instructions may be provided in accordance with the principles described herein. The instructions, when executed by a processor of a computing device, may direct the processor and/or computing device to perform one or more operations, including one or more of the operations described herein. Such instructions may be stored and/or transmitted using any of a variety of known computer-readable media.

A non-transitory computer-readable medium as referred to herein may include any non-transitory storage medium that participates in providing data (e.g., instructions) that may be read and/or executed by a computing device (e.g., by a processor of a computing device). For example, a non-transitory computer-readable medium may include, but is not limited to, any combination of non-volatile storage media and/or volatile storage media. Exemplary non-volatile storage media include, but are not limited to, read-only memory, flash memory, a solid-state drive, a magnetic storage device (e.g. a hard disk, a floppy disk, magnetic tape, etc.), ferroelectric random-access memory ("RAM"), and an optical disc (e.g., a compact disc, a digital video disc, a Blu-ray disc, etc.). Exemplary volatile storage media include, but are not limited to, RAM (e.g., dynamic RAM).

Figure 12:
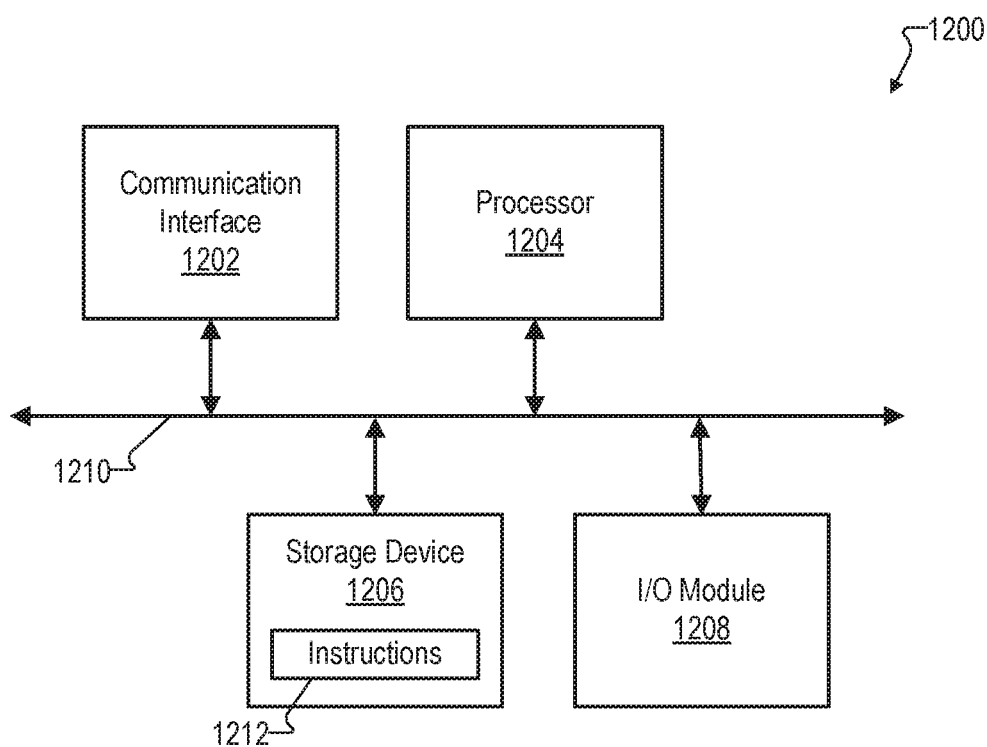
FIG. 12 illustrates an exemplary computing device according to principles described herein.

FIG. 12 illustrates an exemplary computing device 1200 that may be specifically configured to perform one or more of the processes described herein. As shown in FIG. 12, computing device 1200 may include a communication interface 1202, a processor 1204, a storage device 1206, and an input/output ("I/O") module 1208 communicatively connected one to another via a communication infrastructure 1210. While an exemplary computing device 1200 is shown in FIG. 12, the components illustrated in FIG. 12 are not intended to be limiting. Additional or alternative components may be used in other embodiments. Components of computing device 1200 shown in FIG. 12 will now be described in additional detail.

Communication interface 1202 may be configured to communicate with one or more computing devices. Examples of communication interface 1202 include, without limitation, a wired network interface (such as a network interface card), a wireless network interface (such as a wireless network interface card), a modem, an audio/video connection, and any other suitable interface.

Processor 1204 generally represents any type or form of processing unit capable of processing data and/or interpreting, executing, and/or directing execution of one or more of the instructions, processes, and/or operations described herein. Processor 1204 may perform operations by executing computer-executable instructions 1212 (e.g., an application, software, code, and/or other executable data instance) stored in storage device 1206.

Storage device 1206 may include one or more data storage media, devices, or configurations and may employ any type, form, and combination of data storage media and/or device. For example, storage device 1206 may include, but is not limited to, any combination of the non-volatile media and/or volatile media described herein. Electronic data, including data described herein, may be temporarily and/or permanently stored in storage device 1206. For example, data representative of computer-executable instructions 1212 configured to direct processor 1204 to perform any of the operations described herein may be stored within storage device 1206. In some examples, data may be arranged in one or more databases residing within storage device 1206.

I/O module 1208 may include one or more I/O modules configured to receive user input and provide user output. One or more I/O modules may be used to receive input for a single virtual experience. I/O module 1208 may include any hardware, firmware, software, or combination thereof supportive of input and output capabilities. For example, I/O module 1208 may include hardware and/or software for capturing user input, including, but not limited to, a keyboard or keypad, a touchscreen component (e.g., touchscreen display), a receiver (e.g., an RF or infrared receiver), motion sensors, and/or one or more input buttons.

I/O module 1208 may include one or more devices for presenting output to a user, including, but not limited to, a graphics engine, a display (e.g., a display screen), one or more output drivers (e.g., display drivers), one or more audio speakers, and one or more audio drivers. In certain embodiments, I/O module 1208 is configured to provide graphical data to a display for presentation to a user. The graphical data may be representative of one or more graphical user interfaces and/or any other graphical content as may serve a particular implementation.

In some examples, any of the systems, computing devices, and/or other components described herein may be implemented by computing device 1200. For example, storage facility 208 may be implemented by storage device 1206, and processing facility 206 may be implemented by processor 1204.

In the preceding description, various exemplary embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

What is claimed is:

1. An auto-configurable simulation system comprising:
   a control module configured to simulate a first type of surgical instrument manipulating system included in a plurality of types of surgical instrument manipulating systems; and
   a computing device communicatively connected to the control module, the computing device including:
      a memory storing instructions; and
      a processor communicatively connected to the memory and configured to execute the instructions to:
         communicatively connect the control module to a user control console of a computer-assisted surgical system;
         determine, after communicatively connecting the control module to the user control console, that the user control console is configured to facilitate control of a second type of surgical instrument manipulating system included in the plurality of types of surgical instrument manipulating systems;
         store data indicating that the user control console is configured to facilitate control of the second type of surgical instrument manipulating system;
         communicatively disconnect the control module from the user control console after storing the data;
         reprogram the control module such that the control module is configured to simulate the second type of surgical instrument manipulating system; and
         communicatively reconnect the control module to the user control console after reprogramming the control module.

2. The auto-configurable simulation system according to claim 1, wherein:
   the user control console includes an input device and a display device; and
   the processor is further configured to execute the instructions to:
      provide, based on the reprogrammed control module, a virtual environment for display by the display device of the user control console, the virtual environment including a virtual instrument that is movable in response to movement of the input device of the user control console for performing a simulated procedure in the virtual environment.

3. The auto-configurable simulation system according to claim 2, wherein the virtual environment is specific to the second type of surgical instrument manipulating system included in the plurality of types of surgical instrument manipulating systems.

4. The auto-configurable simulation system according to claim 1, wherein:
   the first type of surgical instrument manipulating system has a first manipulator arm configuration;
   the second type of surgical instrument manipulating system has a second manipulator arm configuration; and
   the first manipulator arm configuration is different from the second manipulator arm configuration.

5. The auto-configurable simulation system according to claim 1, wherein the processor is further configured to execute instructions to:
   communicatively connect, after reprogramming the control module and after the control module is disconnected from the user control console, the control module to an additional user control console;
   determine, after communicatively connecting the control module to the additional user control console, that the additional user control console is configured to facilitate control of a third type of surgical instrument manipulating system included in the plurality of types of surgical instrument manipulating systems;
   store data indicating that the additional user control console is configured to facilitate control of the third type of surgical instrument manipulating system; and
   reprogram the control module such that the control module is configured to simulate the third type of surgical instrument manipulating system.

6. The auto-configurable simulation system according to claim 1, wherein:
   the control module includes a plurality of hardware nodes; and
   a hardware node included in the plurality of hardware nodes is configured to simulate a component of the second type of surgical instrument manipulating system.

7. The auto-configurable simulation system according to claim 6, wherein the component is a manipulator arm used in the second type of surgical instrument manipulating system.

8. The auto-configurable simulation system according to claim 1, wherein the reprogramming of the control module includes reprogramming a virtual hardware module included in the control module to simulate a component of the second type of surgical instrument manipulating system.

9. The auto-configurable simulation system according to claim 1, wherein the reprogramming of the control module includes:
accessing, from a plurality of sets of configuration parameters, a set of configuration parameters associated with the second type of surgical instrument manipulating system; and
using the set of configuration parameters associated with the second type of surgical instrument manipulating system to configure the control module to communicate with the user control console.

10. The auto-configurable simulation system according to claim 1, wherein the determining that the user control console is configured to facilitate control of the second type of surgical instrument manipulating system is based on information included in a handshake signal received from the user control console.

11. An auto-configurable simulation system comprising:
a memory storing instructions; and
a processor communicatively connected to the memory and configured to execute the instructions to:
communicatively connect a control module to a user control console that includes an input device and a display device, the control module configured to simulate a first type of surgical instrument manipulating system included in a plurality of types of surgical instrument manipulating systems;
determine, after communicatively connecting the control module to the user control console, that the user control console is configured to facilitate control of a second type of surgical instrument manipulating system included in the plurality of types of surgical instrument manipulating systems;
store data indicating that the user control console is configured to facilitate control of the second type of surgical instrument manipulating system;
communicatively disconnect the control module from the user control console after storing the data;
reprogram the control module such that the control module is configured to simulate the second type of surgical instrument manipulating system;
communicatively reconnect the control module to the user control console after reprogramming the control module; and
provide, based on the reprogrammed control module, a virtual environment for display by the display device of the user control console, the virtual environment including a virtual instrument that is movable in response to movement of the input device of the user control console for performing a simulated procedure in the virtual environment.

12. The auto-configurable simulation system according to claim 11, wherein the virtual environment is specific to the first type of surgical instrument manipulating system included in the plurality of types of surgical instrument manipulating systems.

13. A method comprising:
determining, by an auto-configurable simulation system after a control module configurable to simulate one of a plurality of types of surgical instrument manipulating systems is communicatively connected to a user control console, that the user control console is configured to facilitate control of a first type of surgical instrument manipulating system included in the plurality of types of surgical instrument manipulating systems;
determining, by the auto-configurable simulation system, whether the control module is currently configured to simulate the first type of surgical instrument manipulating system included in the plurality of types of surgical instrument manipulating systems;
storing, by the auto-configurable simulation system when it is determined that the control module is not currently configured to simulate the first type of surgical instrument manipulating system, data indicating that the user control console is configured to facilitate control of the first type of surgical instrument manipulating system;
communicatively disconnecting, by the auto-configurable simulation system after the storing of the data, the control module from the user control console;
reprogramming, by the auto-configurable simulation system when it is determined that the control module is not currently configured to simulate the first type of surgical instrument manipulating system, the control module such that the control module is configured to simulate the first type of surgical instrument manipulating system; and
communicatively reconnecting, by the auto-configurable simulation system after the reprogramming of the control module, the control module to the user control console.

14. The method according to claim 13, further comprising providing, by the auto-configurable simulation system, a virtual environment for display by a display device of the user control console, the virtual environment including a virtual instrument that is movable in response to movement of an input device of the user control console for performing a simulated procedure in the virtual environment.

15. The method according to claim 13, further comprising:
determining, by the auto-configurable simulation system after the control module is disconnected from the user control console and communicatively connected to an additional user control console, that the additional user control console is configured to facilitate control of a second type of surgical instrument manipulating system included in the plurality of types of surgical instrument manipulating systems;
determining, by the auto-configurable simulation system, that the control module is currently configured to simulate the first type of surgical instrument manipulating system included in the plurality of types of surgical instrument manipulating systems; and
reprograming, by the auto-configurable simulation system, the control module such that the control module is configured to simulate the second type of surgical instrument manipulating system instead of the first type of surgical instrument manipulating system.

16. The method according to claim 13, further comprising:
receiving, by the auto-configurable simulation system, a notification indicating that the auto-configurable simulation system will be communicatively connected to a third type of surgical instrument manipulating system in the future; and
reprograming, by the auto-configurable simulation system based on the notification and prior to the control module being communicatively connected to the third type of surgical instrument manipulating system, the control module such that the control module is configured to simulate the third type of surgical instrument manipulating system.

17. An auto-configurable simulation system comprising:
a control module configured to simulate a first type of surgical instrument manipulating system included in a plurality of types of surgical instrument manipulating systems; and
a computing device communicatively connected to the control module, the computing device including:
a memory storing instructions; and
a processor communicatively connected to the memory and configured to execute the instructions to:
communicatively connect the control module to a user control console of a computer-assisted surgical system;
determine, after communicatively connecting the control module to the user control console, that the user control console is configured to facilitate control of a second type of surgical instrument manipulating system included in the plurality of types of surgical instrument manipulating systems;
store data indicating that the user control console is configured to facilitate control of the second type of surgical instrument manipulating system;
reprogram the control module such that the control module is configured to simulate the second type of surgical instrument manipulating system;
communicatively connect, after reprogramming the control module and after the control module is disconnected from the user control console, the control module to an additional user control console;
determine, after communicatively connecting the control module to the additional user control console, that the additional user control console is configured to facilitate control of a third type of surgical instrument manipulating system included in the plurality of types of surgical instrument manipulating systems;
store data indicating that the additional user control console is configured to facilitate control of the third type of surgical instrument manipulating system; and
reprogram the control module such that the control module is configured to simulate the third type of surgical instrument manipulating system.

18. A method comprising:
determining, by an auto-configurable simulation system after a control module configurable to simulate one of a plurality of types of surgical instrument manipulating systems is communicatively connected to a user control console, that the user control console is configured to facilitate control of a first type of surgical instrument manipulating system included in the plurality of types of surgical instrument manipulating systems;
determining, by the auto-configurable simulation system, whether the control module is currently configured to simulate the first type of surgical instrument manipulating system included in the plurality of types of surgical instrument manipulating systems;
reprogramming, by the auto-configurable simulation system when it is determined that the control module is not currently configured to simulate the first type of surgical instrument manipulating system, the control module such that the control module is configured to simulate the first type of surgical instrument manipulating system;
determining, by the auto-configurable simulation system after the control module is disconnected from the user control console and communicatively connected to an additional user control console, that the additional user control console is configured to facilitate control of a second type of surgical instrument manipulating system included in the plurality of types of surgical instrument manipulating systems;
determining, by the auto-configurable simulation system, that the control module is currently configured to simulate the first type of surgical instrument manipulating system included in the plurality of types of surgical instrument manipulating systems; and
reprogramming, by the auto-configurable simulation system, the control module such that the control module is configured to simulate the second type of surgical instrument manipulating system instead of the first type of surgical instrument manipulating system.

19. A method comprising:
determining, by an auto-configurable simulation system after a control module configurable to simulate one of a plurality of types of surgical instrument manipulating systems is communicatively connected to a user control console, that the user control console is configured to facilitate control of a first type of surgical instrument manipulating system included in the plurality of types of surgical instrument manipulating systems;
determining, by the auto-configurable simulation system, whether the control module is currently configured to simulate the first type of surgical instrument manipulating system included in the plurality of types of surgical instrument manipulating systems;
reprogramming, by the auto-configurable simulation system when it is determined that the control module is not currently configured to simulate the first type of surgical instrument manipulating system, the control module such that the control module is configured to simulate the first type of surgical instrument manipulating system;
receiving, by the auto-configurable simulation system, a notification indicating that the auto-configurable simulation system will be communicatively connected to a third type of surgical instrument manipulating system in the future; and
reprograming, by the auto-configurable simulation system based on the notification and prior to the control module being communicatively connected to the third type of surgical instrument manipulating system, the control module such that the control module is configured to simulate the third type of surgical instrument manipulating system.

* * * * *